United States Patent
Flaherty et al.

(10) Patent No.: US 6,723,072 B2
(45) Date of Patent: Apr. 20, 2004

(54) PLUNGER ASSEMBLY FOR PATIENT INFUSION DEVICE

(75) Inventors: J. Christopher Flaherty, Topsfield, MA (US); Christopher Carter Gregory, Newtown, PA (US); Derek Dwayne Mahoney, Manalapan, NJ (US); John Michael Margicin, Levittown, PA (US)

(73) Assignee: Insulet Corporation, Beverly, MA (US)

( * ) Notice: Subject to any disclaimer, the term of this patent is extended or adjusted under 35 U.S.C. 154(b) by 40 days.

(21) Appl. No.: 10/163,690

(22) Filed: Jun. 6, 2002

(65) Prior Publication Data

US 2003/0229310 A1 Dec. 11, 2003

(51) Int. Cl.⁷ .................. A61M 31/00; A61M 37/00
(52) U.S. Cl. ............................. 604/131; 604/67
(58) Field of Search ................. 604/132, 141, 604/135, 20, 155, 142, 131, 288.01, 506, 65, 143, 67

(56) References Cited

U.S. PATENT DOCUMENTS

| | | |
|---|---|---|
| 3,631,847 A | 1/1972 | Hobbs |
| 3,812,843 A | 5/1974 | Wootten et al. |
| 3,885,662 A | 5/1975 | Schaefer |
| 4,067,000 A | 1/1978 | Carlson |
| 4,108,177 A | 8/1978 | Pistor |
| 4,151,845 A | 5/1979 | Clemens |
| 4,211,998 A | 7/1980 | Junginger et al. |
| 4,231,019 A | 10/1980 | Junginger et al. |
| 4,268,150 A | 5/1981 | Chen |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |

(List continued on next page.)

FOREIGN PATENT DOCUMENTS

| | | |
|---|---|---|
| DE | 4200595 | 7/1993 |
| DE | 19920896 | 9/2000 |
| EP | 0342947 | 5/1989 |
| EP | 0763369 | 3/1997 |
| EP | 0867196 | 3/1998 |

(List continued on next page.)

OTHER PUBLICATIONS

US 5,954,699, 9/1999, Jost et al. (withdrawn)
Web–Site Brochure dated Jan. 4, 2000. MiniMed 508. "Doing its job. Naturally." www.minimed.com/tiles/mm_113.htm.

(List continued on next page.)

Primary Examiner—Brian L. Casler
Assistant Examiner—Roz Ghafoorian
(74) Attorney, Agent, or Firm—McDermott Will & Emery

(57) ABSTRACT

A device for delivering fluid, such as insulin, to a patient. The device includes an exit port assembly, a syringe-like reservoir including a side wall extending along a longitudinal axis towards an outlet connected to the exit port assembly, and a plunger assembly received in the reservoir. The plunger assembly includes a two-way shape memory element connecting first and second lateral segments, and having a changeable length decreasing from an uncharged length to a charged length when at least one charge is applied to the shape memory element. Successively applying a charge and removing the charge from the two-way shape memory element causes longitudinal movement of the plunger assembly towards the outlet of the reservoir in order to cause fluid to be dispensed from the reservoir to the exit port assembly.

22 Claims, 16 Drawing Sheets

U.S. PATENT DOCUMENTS

| | | |
|---|---|---|
| 4,498,843 A | 2/1985 | Schneider et al. |
| 4,514,732 A | 4/1985 | Hayes, Jr. |
| 4,529,401 A | 7/1985 | Leslie et al. |
| 4,559,033 A | 12/1985 | Stephen et al. |
| 4,559,037 A | 12/1985 | Franetzki et al. |
| 4,560,979 A | 12/1985 | Rosskopf |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| D303,013 S | 8/1989 | Konopka |
| 4,855,746 A | 8/1989 | Stacy |
| 4,882,600 A | 11/1989 | Van de Moere |
| 4,886,499 A | 12/1989 | Cirelli et al. |
| 4,898,579 A | 2/1990 | Groshong et al. |
| D306,691 S | 3/1990 | Arai |
| D311,735 S | 10/1990 | Arai et al. |
| 4,969,874 A | 11/1990 | Michel et al. |
| 4,973,998 A | 11/1990 | Gates |
| D315,727 S | 3/1991 | Arai et al. |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,176,662 A | 1/1993 | Bartholomew et al. |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,242,406 A | 9/1993 | Gross et al. |
| 5,244,463 A | 9/1993 | Cordner, Jr. et al. |
| 5,245,447 A | 9/1993 | Stemmle |
| 5,254,096 A | 10/1993 | Rondelet et al. |
| 5,257,980 A | 11/1993 | Van Antwerp et al. |
| 5,281,202 A | 1/1994 | Weber et al. |
| 5,312,337 A | 5/1994 | Flaherty et al. |
| 5,318,540 A | 6/1994 | Athayde et al. |
| 5,342,313 A | 8/1994 | Campbell et al. |
| 5,411,480 A | 5/1995 | Kriesel |
| 5,433,710 A | 7/1995 | Van Antwerp et al. |
| 5,452,033 A | 9/1995 | Balling et al. |
| 5,492,534 A | 2/1996 | Athayde et al. |
| 5,505,709 A | 4/1996 | Funderburk et al. |
| 5,507,288 A | 4/1996 | Bocker et al. ............... 128/633 |
| 5,514,096 A | 5/1996 | Hiejima |
| 5,533,389 A | 7/1996 | Kamen et al. |
| 5,545,152 A | 8/1996 | Funderburk et al. |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,660,728 A | 8/1997 | Saaski et al. |
| 5,665,065 A | 9/1997 | Colman et al. |
| 5,665,070 A | 9/1997 | McPhee |
| 5,695,490 A | 12/1997 | Flaherty et al. |
| 5,702,363 A | 12/1997 | Flaherty |
| 5,704,520 A | 1/1998 | Gross |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | McPhee |
| 5,810,015 A | 9/1998 | Flaherty |
| 5,814,020 A | 9/1998 | Gross |
| 5,839,467 A | 11/1998 | Saaski et al. |
| 5,840,063 A | 11/1998 | Flaherty |
| 5,845,218 A | 12/1998 | Altschul |
| 5,848,991 A | 12/1998 | Gross et al. |
| 5,851,197 A | 12/1998 | Marano et al. |
| 5,858,001 A * | 1/1999 | Tsals et al. ................. 604/135 |
| 5,858,005 A | 1/1999 | Kriesel |
| D405,524 S | 2/1999 | Falk et al. |
| 5,875,393 A | 2/1999 | Altschul et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,935,099 A | 8/1999 | Peterson et al. |
| 5,954,058 A | 9/1999 | Flaherty |
| 5,957,890 A | 9/1999 | Mann et al. |
| 5,965,848 A | 10/1999 | Altschul et al. |
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,061,580 A | 5/2000 | Altschul et al. |
| 6,071,292 A | 6/2000 | Makower et al. |
| 6,144,847 A | 11/2000 | Altschul et al. |
| 6,152,898 A | 11/2000 | Olsen |
| 6,363,609 B1 | 4/2002 | Pickren |
| 6,375,638 B2 | 4/2002 | Nason et al. |
| 6,485,461 B1 * | 11/2002 | Mason et al. ............... 604/132 |
| 6,520,936 B1 * | 2/2003 | Mann ........................ 604/141 |

FOREIGN PATENT DOCUMENTS

| | | |
|---|---|---|
| EP | 0937475 | 8/1999 |
| WO | WO81/01658 | 6/1981 |
| WO | WO86/06796 | 11/1986 |
| WO | WO98/00193 | 1/1998 |
| WO | WO98/01071 | 1/1998 |
| WO | WO00/19887 | 9/1999 |
| WO | WO99/56803 | 11/1999 |
| WO | WO99/62576 | 12/1999 |
| WO | WO0010628 | 3/2000 |
| WO | WO00/29047 | 5/2000 |
| WO | WO00/29049 | 5/2000 |
| WO | WO00/74752 | 5/2000 |
| WO | WO00/30705 | 6/2000 |
| WO | WO00/78210 | 6/2000 |
| WO | WO00/48112 | 8/2000 |
| WO | WO00/61215 | 10/2000 |
| WO | WO01/52727 | 1/2001 |
| WO | WO01/5663 | 8/2001 |
| WO | WO01/76684 | 10/2001 |
| WO | WO02/20073 | 3/2002 |

OTHER PUBLICATIONS

Web–Site Brochure dated Dec. 20, 1999. Applied Medical Technology. "508 Pump Information". www.applied-medical.co.uk/508.htm.
Web–Site Brochure dated Jan. 4, 2000. "The Glucose Sensor". www.animascorp.com/sensor_f.html.
Web–Site Brochure dated Dec. 20, 1999. "The Animas R–1000 Insulin Pump". www.animascorp.com/pump_f_s.html.
Web–Site Brochure dated Dec. 20, 1999. "The Animas R–1000 Insulin Pump". www.animascorp.com/pump_f_f.html.
Web–Site Brochure dated Jan. 4, 2000. SOOIL–Homepage. "Portable Insulin Pump". www.sooil.com/intro2.htm.
Web–Site Brochure dated Jan. 4, 2000. SOOIL–Homepage. "Portable Insulin Pump". www.sooil.com/product2.htm.
Web–Site Brochure dated Jan. 4, 2000. SOOIL–Homepage. "Portable Insulin Pump". www.sooil.com/product3.htm.
Web–Site Brochure dated Jan. 4, 2000. SOOIL–Homepage. "Portable Insulin Pump". www.sooil.com/product4.htm.
User's Guide for Model 508 Insulin Pump, MiniMed, 8/00, 145 pages.
Copy of PCT International Search Report dated Mar. 4, 2002; 5pp.
Morgan Electro Ceramics; Piezo Ceramics Products Technical Information; *Instruction Piezoelectric Ceramics,* May 16, 2001; 15 pages.
Solenoids Catalog—Magnetic Sensor Systems, *Solenoid Construction,* 2 pages.
Lind et al, 2nd Tampere International Conference on Machine Automation; *Linear Motion Miniature Actuators,* Sep., 1998; 12 pages.
Galante, T., et al; United Technologies Research Center, ; *Design, Modeling, and Performance of a High Force Piezoelectric Inchworm Motor,* 13 pages.
M. Vaughan; Thesis submitted to the Faculty of the Virginia Polytechnic Institute and State University; *The Design, Fabrication, and Modeling of a Piezoelectric Linear Motor,* Dec. 2001.
Mavroidis, C.; Department of Mechanical and Aerospace Engineering, Rutgers University, *Development of Advanced Actuators Using Shape Memory Alloys and Electrorheological Fluids,* 70 pages.
Park, J., et al, Mechanical and Aerospace Engineering Dept., University of California, *Design and Testing of a Mesoscale Actuator Device,* 33 Pages.

* cited by examiner

PLUNGER ASSEMBLY FOR PATIENT INFUSION DEVICE

CROSS-REFERENCE TO RELATED APPLICATIONS

The present application is related to co-pending U.S. patent application Ser. No. 10/163,688, which was filed on the same day as the present application, is also entitled PLUNGER ASSEMBLY FOR PATIENT INFUSION DEVICE, and is assigned to the assignee of the present application and incorporated herein by reference.

The present application is also related to co-pending U.S. patent application Ser. No. 09/943,992, filed on Aug. 31, 2001, and entitled DEVICES, SYSTEMS AND METHODS FOR PATIENT INFUSION, which is assigned to the assignee of the present application and incorporated herein by reference.

FIELD OF THE INVENTION

The present invention relates generally to medical devices, systems and methods, and more particularly to small, low cost, portable infusion devices and methods that are useable to achieve precise, sophisticated, and programmable flow patterns for the delivery of therapeutic liquids such as insulin to a mammalian patient. Even more particularly, the present invention is directed to a plunger assembly for a fluid delivery device, that utilizes a two-way shape memory element.

BACKGROUND OF THE INVENTION

Today, there are numerous diseases and other physical ailments that are treated by various medicines including pharmaceuticals, nutritional formulas, biologically derived or active agents, hormonal and gene based material and other substances in both solid or liquid form. In the delivery of these medicines, it is often desirable to bypass the digestive system of a mammalian patient to avoid degradation of the active ingredients caused by the catalytic enzymes in the digestive tract and liver. Delivery of a medicine other than by way of the intestines is known as parenteral delivery. Parenteral delivery of various drugs in liquid form is often desired to enhance the effect of the substance being delivered, insuring that the unaltered medicine reaches its intended site at a significant concentration. Also, undesired side effects associated with other routes of delivery, such as systemic toxicity, can potentially be avoided.

Often, a medicine may only be available in a liquid form, or the liquid version may have desirable characteristics that cannot be achieved with solid or pill form. Delivery of liquid medicines may best be accomplished by infusing directly into the cardiovascular system via veins or arteries, into the subcutaneous tissue or directly into organs, tumors, cavities, bones or other site specific locations within the body.

Parenteral delivery of liquid medicines into the body is often accomplished by administering bolus injections using a needle and reservoir, or continuously by gravity driven dispensers or transdermal patch technologies. Bolus injections often imperfectly match the clinical needs of the patient, and usually require larger individual doses than are desired at the specific time they are given. Continuous delivery of medicine through gravity feed systems compromise the patient's mobility and lifestyle, and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. An example of a use of an ambulatory infusion pump is for the delivery of insulin for the treatment of diabetes mellitus. These pumps can deliver insulin on a continuous basal basis as well as a bolus basis as is disclosed in U.S. Pat. No. 4,498,843 to Schneider et al.

The ambulatory pumps often work with a reservoir to contain the liquid medicine, such as a cartridge, a syringe or an IV bag, and use electromechanical pumping or metering technology to deliver the medication to the patient via tubing from the infusion device to a needle that is inserted transcutaneously, or through the skin of the patient. The devices allow control and programming via electromechanical buttons or switches located on the housing of the device, and accessed by the patient or clinician. The devices include visual feedback via text or graphic screens, such as liquid crystal displays known as LCD's, and may include alert or warning lights and audio or vibration signals and alarms. The device can be worn in a harness or pocket or strapped to the body of the patient.

Currently available ambulatory infusion devices are expensive, difficult to program and prepare for infusion, and tend to be bulky, heavy and very fragile. Filling these devices can be difficult and require the patient to carry both the intended medication as well as filling accessories. The devices require specialized care, maintenance, and cleaning to assure proper functionality and safety for their intended long term use. Due to the high cost of existing devices, healthcare providers limit the patient populations approved to use the devices and therapies for which the devices can be used.

Clearly, therefore, there was a need for a programmable and adjustable infusion system that is precise and reliable and can offer clinicians and patients a small, low cost, light-weight, easy-to-use alternative for parenteral delivery of liquid medicines.

In response, the applicant of the present application provided a small, low cost, light-weight, easy-to-use device for delivering liquid medicines to a patient. The device, which is described in detail in co-pending U.S. application Ser. No. 09/943,992, filed on Aug. 31, 2001, includes an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. To reduce the size, complexity and costs of the device, the device is provided with a housing that is free of user input components, such as a keypad, for providing flow instructions to the local processor.

What are still desired are new and improved components, such as plunger assemblies and reservoirs, for a device for delivering fluid to a patient. Preferably, the components will be simple in design, and relatively compact, light-weight, easy to manufacture and inexpensive, such that the resulting fluid delivery device can be effective, yet inexpensive and disposable.

SUMMARY OF THE INVENTION

The present invention provides a device for delivering fluid, such as insulin for example, to a patient. The device includes an exit port assembly, and a reservoir including an outlet connected to the exit port assembly and a side wall extending along a longitudinal axis towards the outlet. A plunger assembly is received in the reservoir and is movable along the longitudinal axis of the reservoir towards the outlet of the reservoir.

The plunger assembly includes a first lateral segment extending laterally with respect to the longitudinal axis of the reservoir and contacting the side wall of the reservoir, and a second lateral segment extending laterally with respect to the longitudinal axis of the reservoir and contacting the side wall of the reservoir. The second lateral segment is positioned between the first lateral segment and the outlet of the reservoir and is longitudinally spaced from the first lateral segment. The plunger assembly also includes an elongated two-way shape memory element extending substantially parallel with respect to the longitudinal axis of the reservoir and connecting the first and the second lateral segments.

The two-way shape memory element has a changeable length decreasing from an uncharged length to a charged length when at least one charge is applied to the shape memory element. Successively applying and removing charges to the shape memory element causes the plunger assembly to intermittently advance longitudinally within the reservoir to force fluid through the outlet of the resrevoir.

The present invention, therefore, provides a device for delivering fluid to a patient including new and improved components, such as plunger assemblies utilizing two-way shape memory elements. The components are simple in design, and relatively compact, lightweight, and easy to manufacture and inexpensive, such that the resulting fluid delivery device is also relatively compact, light-weight, easy to manufacture and inexpensive.

These aspects of the invention together with additional features and advantages thereof may best be understood by reference to the following detailed descriptions and examples taken in connection with the accompanying illustrated drawings.

BRIEF DESCRIPTION OF THE DRAWINGS

Like reference characters designate identical or corresponding components and units throughout the several views.

DETAILED DESCRIPTION OF EXEMPLARY EMBODIMENTS

Figure 2:
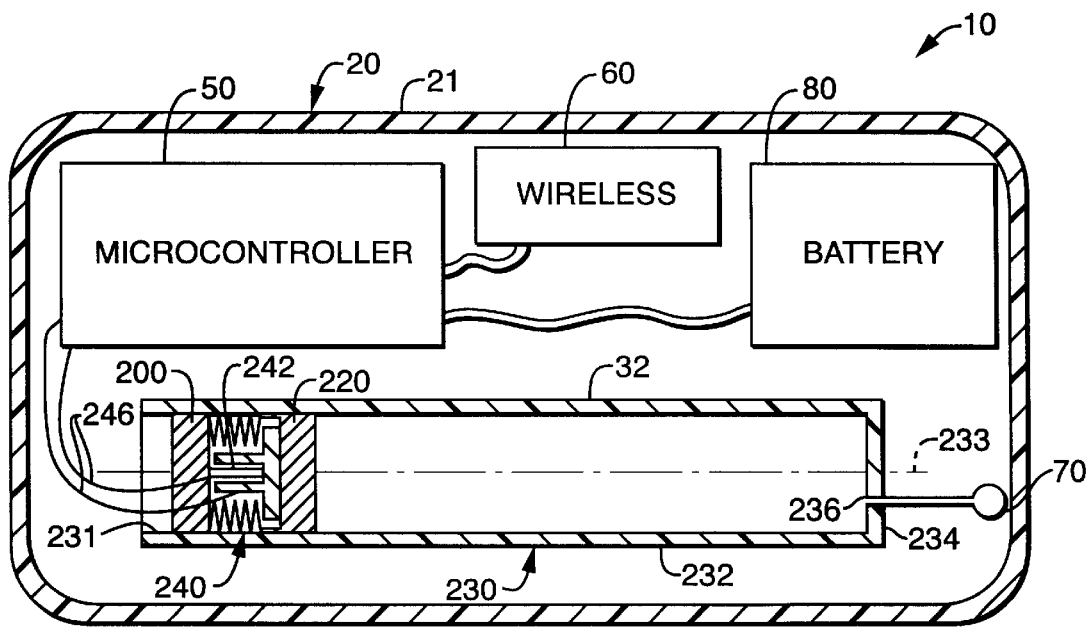
FIG. 2 is a sectional side view of the fluid delivery device of FIG. 1 showing an exemplary embodiment of a plunger assembly constructed in accordance with the present invention for causing fluid to be dispensed from the device.

Referring first to FIG. 2, there is illustrated an exemplary embodiment of a fluid delivery device 10 including a dispenser in the form of a plunger assembly 240 constructed in accordance with the present invention. The plunger assembly 240 causes fluid flow from a reservoir 230 to an exit port assembly 70 during operation of the device 10. In general, the plunger assembly 240 utilizes a two-way shape memory element in accordance with the present invention to provide effective, yet simple and inexpensive fluid dispensing for the fluid delivery device 10.

The fluid delivery device 10 of FIG. 2 can be used for the delivery of fluids to a person or animal. The types of liquids that can be delivered by the fluid delivery device 10 include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery device 10 might be used to treat include, but are not limited to, diabetes, cardiovascular disease, pain, chronic pain, cancer, AIDS, neurological diseases, Alzheimer's Disease, ALS, Hepatitis, Parkinson's Disease or spasticity. In addition, it should be understood that the plunger assembly 240 according to the present invention can be used with fluid delivery devices other than those used for the delivery of fluids to persons or animals.

Figure 1:
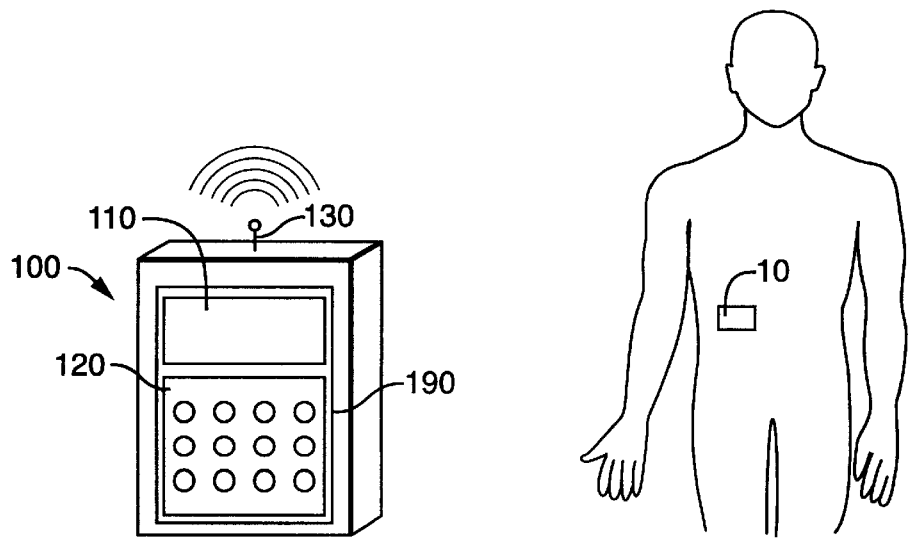
FIG. 1 is a perspective view of a first exemplary embodiment of a fluid delivery device constructed in accordance with the present invention and shown secured on a patient, and a remote control device for use with the fluid delivery device (the remote control device being enlarged with respect to the patient and the fluid delivery device for purposes of illustration)

The fluid delivery device 10 also includes a processor or electronic microcontroller (hereinafter referred to as the "local" processor) 50 connected to the plunger assembly 240. The local processor 50 is programmed to cause a flow of fluid to the exit port assembly 70 based on flow instructions from a separate, remote control device 100, an example of which is shown in FIG. 1. Referring also to FIG. 2, the fluid delivery device 10 further includes a wireless receiver 60 connected to the local processor 50 for receiving the flow instructions from the separate, remote control device 100 and delivering the flow instructions to the local processor. The device 10 also includes a housing 20 containing the exit port assembly 70, the reservoir 230, the plunger assembly 240, the local processor 50 and the wireless receiver 60.

As shown, the housing 20 of the fluid delivery device 10 is free of user input components for providing flow instructions to the local processor 50, such as electromechanical switches or buttons on an outer surface 21 of the housing, or interfaces otherwise accessible to a user to adjust the programmed flow rate through the local processor 50. The lack of user input components allows the size, complexity and costs of the device 10 to be substantially reduced so that the device 10 lends itself to being small and disposable in nature. Examples of such devices are disclosed in co-pending U.S. patent application Ser. No. 09/943,992, filed on Aug. 31, 2001, and entitled DEVICES, SYSTEMS AND METHODS FOR PATIENT INFUSION, which is assigned to the assignee of the present application and has previously been incorporated herein by reference.

In order to program, adjust the programming of, or otherwise communicate user inputs to the local processor 50, the fluid delivery device 10 includes the wireless communication element, or receiver 60 for receiving the user inputs from the separate, remote control device 100 of FIG. 1. Signals can be sent via a communication element (not shown) of the remote control device 100, which can include or be connected to an antenna 1230, shown in FIG. 1 as being external to the device 100.

The remote control device 100 has user input components, including an array of electromechanical switches, such as the membrane keypad 120 shown. The control device 100 also includes user output components, including a visual display, such as a liquid crystal display (LCD) 110. Alternatively, the control device can be provided with a touch screen for both user input and output. Although not shown in FIG. 1, the remote control device 100 has its own processor (hereinafter referred to as the "remote" processor) connected to the membrane keypad 120 and the LCD 110. The remote processor receives the user inputs from the membrane keypad 120 and provides "flow" instructions for transmission to the fluid delivery device 10, and provides information to the LCD 110. Since the remote control device 100 also includes a visual display 110, the fluid delivery device 10 can be void of an information screen, further reducing the size, complexity and costs of the device 10.

The communication element 60 of the device 10 preferably receives electronic communication from the remote control device 100 using radio frequency or other wireless communication standards and protocols. In a preferred embodiment, the communication element 60 is a two-way communication element, including a receiver and a transmitter, for allowing the fluid delivery device 10 to send information back to the remote control device 100. In such an embodiment, the remote control device 100 also includes an integral communication element comprising a receiver and a transmitter, for allowing the remote control device 100 to receive the information sent by the fluid delivery device 10.

The local processor 50 of the device 10 contains all the computer programs and electronic circuitry needed to allow a user to program the desired flow patterns and adjust the program as necessary. Such circuitry can include one or more microprocessors, digital and analog integrated circuits, resistors, capacitors, transistors and other semiconductors and other electronic components known to those skilled in the art. The local processor 50 also includes programming, electronic circuitry and memory to properly activate the plunger assembly 240 at the needed time intervals.

In the exemplary embodiment of FIG. 2, the device 10 includes a power supply 80, such as a battery or capacitor, for supplying power to the local processor 50. The power supply 80 is preferably integrated into the fluid delivery device 10, but can be provided as replaceable, e.g., a replaceable battery.

The device 10 can include sensors or transducers such as a reservoir volume transducer or a reservoir pressure transducer, for transmitting information to the local processor 50 to indicate how and when to activate the plunger assembly 240, or to indicate other parameters determining flow, pump flow path prime condition, blockage in flow path, contact sensors, rotary motion or other motion indicators, as well as conditions such as the reservoir 230 being empty or leaking, or the dispensing of too much or too little fluid from the reservoir, etc.

The volume of the reservoir 230 is chosen to best suit the therapeutic application of the fluid delivery device 10 impacted by such factors as available concentrations of medicinal fluids to be delivered, acceptable times between refills or disposal of the fluid delivery device 10, size constraints and other factors. The reservoir 230 may be prefilled by the device manufacturer or a cooperating drug manufacturer, or may include external filling means, such as a fill port. In addition, or alternatively, the device 10 can be provided with a removable and replaceable reservoir.

The exit port assembly 70 can include elements to-penetrate the skin of the patient, such that the entire volume of the flow path of the fluid delivery device 10 is predetermined. For example, a needle-connection tubing terminating in a skin penetrating cannula (not shown) can be provided as in integral part of the exit port assembly 70, with the skin penetrating cannula comprising a rigid member, such as a needle. The exit port assembly 70 can further be provided with injection means, such as a spring driven mechanism, to assist in penetrating the skin with the skin penetrating cannula. For example, if the cannula is a flexible tube, a rigid penetrator within the lumen of the tube can be driven through the skin by the injection means and then withdrawn, leaving the soft cannula in place in the subcutaneous tissue of the patient or other internal site. The injection means may be integral to the device 10, or removable soon after transcutaneous penetration.

Alternatively, the exit port assembly 70 can be adapted to connect, with a Luer connector for example, to a separate, standard infusion device that includes a skin penetrating cannula. In any event, the exit port assembly 70 can also be provided with a removable plug (not shown) for preventing leakage during storage and shipment if pre-filled, and during priming if filled by user, and prior to use. It should be understood that, as used herein, the term "flow path" is meant to include all portions of the fluid delivery device 10 that contain therapeutic fluid for delivery to a patient, e.g., all portions between the fill port of the reservoir to the tip of the needle of the exit port assembly.

The device 10 can also be provided with an adhesive layer on the outer surface of the housing 20 for securing the device 10 directly to the skin of a patient. The adhesive layer is preferably provided in a continuous ring encircling the exit port assembly 70 in order to provide a protective seal around the penetrated skin. The housing 20 can be made from flexible material, or can be provided with flexible hinged sections that allow the fluid delivery device 10 to flex during patient movement to prevent detachment and aid in patient comfort.

Referring to FIGS. 2 and 2a–2c, the present disclosure provides the plunger assembly 240 and the reservoir 230 for use with the fluid delivery device 10 of FIGS. 1 and 2. The plunger assembly 240 is small and simple in design, and inexpensive and easy to manufacture, in order to further reduce the size, complexity and costs of the fluid delivery device 10, such that the device 10 continues to lend itself to being small and disposable in nature. In general, the device 10 is provided with a non-pressurized, syringe-like reservoir 230, and the plunger assembly 240 operates to cause flow from the reservoir 240 to the exit port assembly 70. The plunger assembly 240 is controlled by the local processor 50, which includes electronic programming, controls, and circuitry to allow sophisticated fluid delivery programming and control of the plunger assembly 240.

Referring to FIG. 2, the syringe-like reservoir 230 is provided with a side wall 232 extending along a longitudinal axis 233 between an open end 231 and an end wall 234 of the reservoir. The end wall 234 includes an outlet 236 connected through a first lumen 72 to the exit port assembly 70. The plunger assembly 240 is received in the reservoir 230 and is shaped and sized such that a fluid-tight seal is generally formed between at least a portion of the plunger assembly 240 and the side wall 232 of the reservoir 230 so that movement of the plunger assembly 240 towards the end wall 234 of the reservoir 230 forces fluid through the outlet 236 to the exit port assembly 70.

If desired, the plunger assembly 240 can be prevented from rotating with respect to the side wall 232 of the reservoir 230. For example, the reservoir 230 and the plunger assembly 240 can be provided with matching non-circular cross-sections, such as oval cross-sections. Alternatively, the plunger assembly 240 can be provided with at least one longitudinal channel and the side wall 232 of the reservoir 230 can be provided with at least one protrusion extending longitudinally along its length and received within the channel of the plunger assembly (or vice versa) to prevent rotation of the plunger assembly. In addition, the reservoir 230 and the plunger assembly 240 can alternatively be provided with other matching non-circular cross-sections, such as oval, square or rectangular, along at least a portion of their length to prevent rotation of the plunger assembly 240 with respect to the side wall 232, without the use of a protrusion and a channel. Such non-circular cross-sections can also include simply providing the side wall 232 and the plunger assembly 240 with mating flat portions in otherwise circular cross-sections. The side wall 232 and the end wall 234 of the reservoir are preferably made from a rigid material such as a suitable metal (e.g., stainless steel) or plastic. The plunger assembly 240, however, does not need to be prevented from rotating with respect to the side wall 232.

The plunger assembly 240 includes a first lateral segment 200 extending laterally with respect to the longitudinal axis 233 of the reservoir 230 and contacting the side wall 232 of the reservoir, and a second lateral segment 220 extending laterally with respect to the longitudinal axis 233 of the reservoir 230 and contacting the side wall 232 of the reservoir. The second lateral segment 220 is positioned between the first lateral segment 200 and the outlet 236 of the reservoir 230 and is longitudinally spaced from the first lateral segment 200. The plunger assembly 240 also includes a shape memory element 242 connecting the first and the second lateral segments 200, 220.

The application of an electrical current to the shape memory element 242 heats the material and results in molecular and crystalline restructuring of the shape memory material. If the shape memory material is in the shape of an elongated wire, for example, as the shape memory element 242 preferably is, this restructuring causes a decrease in length. Nitinol, a well-known alloy of nickel and titanium, is an example of such a so-called shape memory material and is preferred for use as the shape memory element 242.

In general, when a piece of elongated shape memory material is in its martensitic form (i.e., low temperature state), it is easily deformed from a shorter length to a longer length. However, when the shape memory material is heated through its transformation temperatures, the shape memory material reverts to its austenite form (i.e., high temperature state) and recovers its shorter length with great force. The temperature (or the level of electrical charge) at which the shape memory material remembers its high temperature form can be adjusted by slight changes in material composition and through heat treatment. In the nickel-titanium alloys, for instance, austenite temperature can be changed from above 100° C. to below 100° C. The shape recovery process occurs over a range of just a few degrees and the start or finish of the transformation can be controlled to within a degree or two if necessary.

These unique shape memory materials, or alloys, also show a superelastic behavior if deformed at a temperature which is slightly above their transformation temperatures. This effect is caused by the stress-induced formation of some martensite above its normal temperature. Because the martensite has been formed above its normal temperature, the martensite reverts immediately to undeformed austenite as soon as the stress is removed. This process provides a very springy, "rubberlike" elasticity in these shape memory materials. A one-way shape memory material can be deformed, then recover to retain permanently its original shape when heated to a certain temperature. A two-way shape memory material, however, holds its original shape at one temperature and takes on another shape at a different temperature. Two-way shape memory material is unique in that the material "remembers" different high temperature and low temperature shapes.

The shape memory element 242 of the embodiment of the present invention comprises an elongated, two-way shape memory material. As shown FIGS. 2 and 2a–2c, the elongated shape memory element 242 is secured between the first and the second lateral segments 200, 220 of the plunger assembly 240 and extends generally parallel to the axis 233 of the reservoir 230. As shown in FIG. 2, the fluid delivery device 10 includes wires 246 connecting opposite ends of the shape memory element 242 to the processor 50, such that the processor can apply electrical charges to the shape memory element 242.

When a charge is applied to the elongated shape memory element 242 through the wires 246, the length of the shape memory element 242 decreases from an uncharged length to a charged length. The shape memory element 242 is arranged such that the changeable length of the shape memory element 242 decreasing from an uncharged length to a charged length causes the first and the second lateral segments 200, 220 to be drawn together, as shown in FIG. 2b. When the charge is removed from the elongated shape memory element 242, the length of the shape memory element 242 increases from the charged length to the uncharged length and causes the first and the second lateral segments 200, 220 to be biased apart, as shown in FIGS. 2a and 2c.

In the embodiment of FIGS. 2 and 2a–2c, the first and the second lateral segments 200, 220 are each sized and shaped to frictionally engage the side wall 232 of the reservoir 230. Moreover, in the embodiment shown the lateral segments 200, 220 each include outer circumferential ridges 205, 225 shaped and oriented to engage the side wall 232 of the reservoir and substantially prevent longitudinal movement of the lateral segments 200, 220 away from the outlet 236 of the reservoir. The frictional engagement force of the lateral segments 200, 220 against the side wall 232 are designed to be slightly less than the force generated by the shape memory element 242 upon changing length.

The plunger assembly 240 also includes a rigid, longitudinally extending projection 248 that limits the smallest longitudinal distance that can be attained between the first and the second lateral segments 200, 220 upon actuation of the shape memory element 242 (i.e., when the first and the second lateral segments 200, 220 are pulled together by the charged shape memory element 242). The differences in lengths between the fully elongated and uncharged shape memory element 242 and the longitudinally extending projection 248 defines the distance traveled by the plunger assembly 240 upon being charged and then uncharged, as described in greater detail below.

Figure 2A:
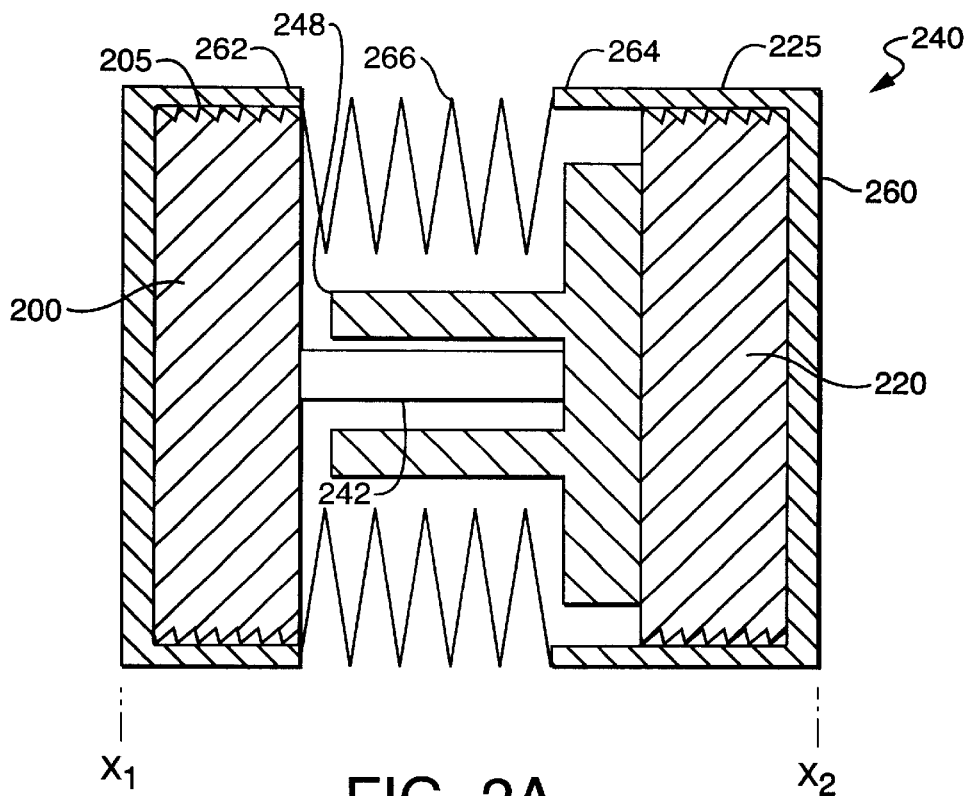
FIGS. 2a–2c are enlarged sectional side views illustrating operation of the plunger assembly of FIG. 2.
Figure 2B:
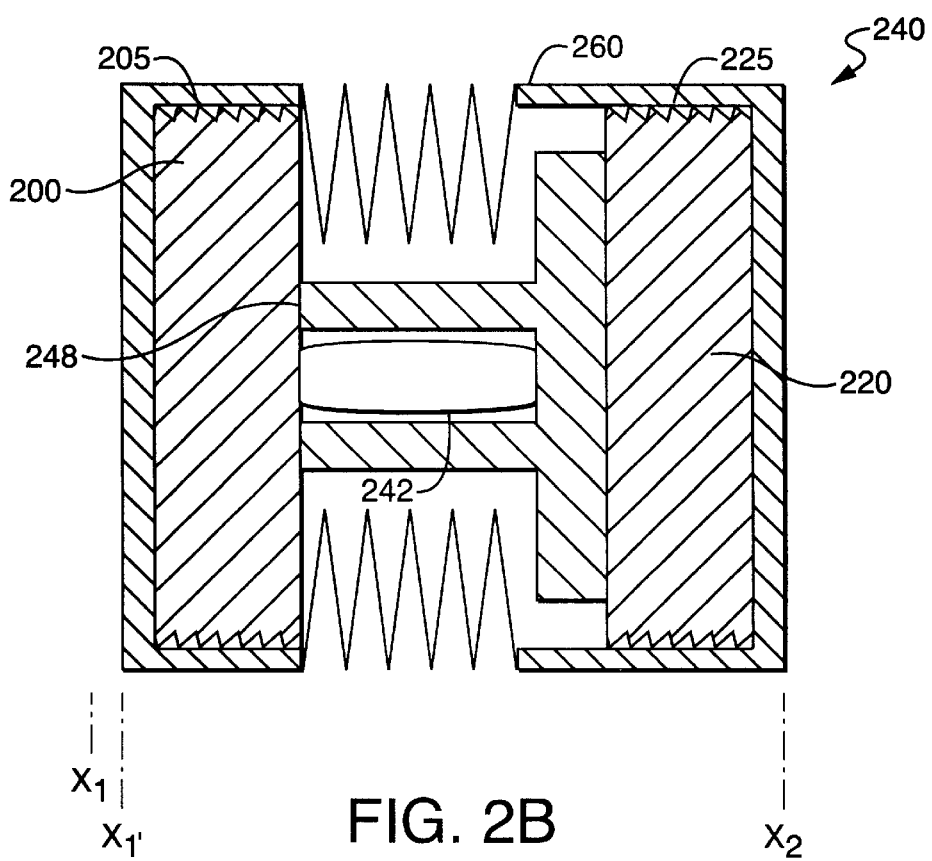
Figure 2C:
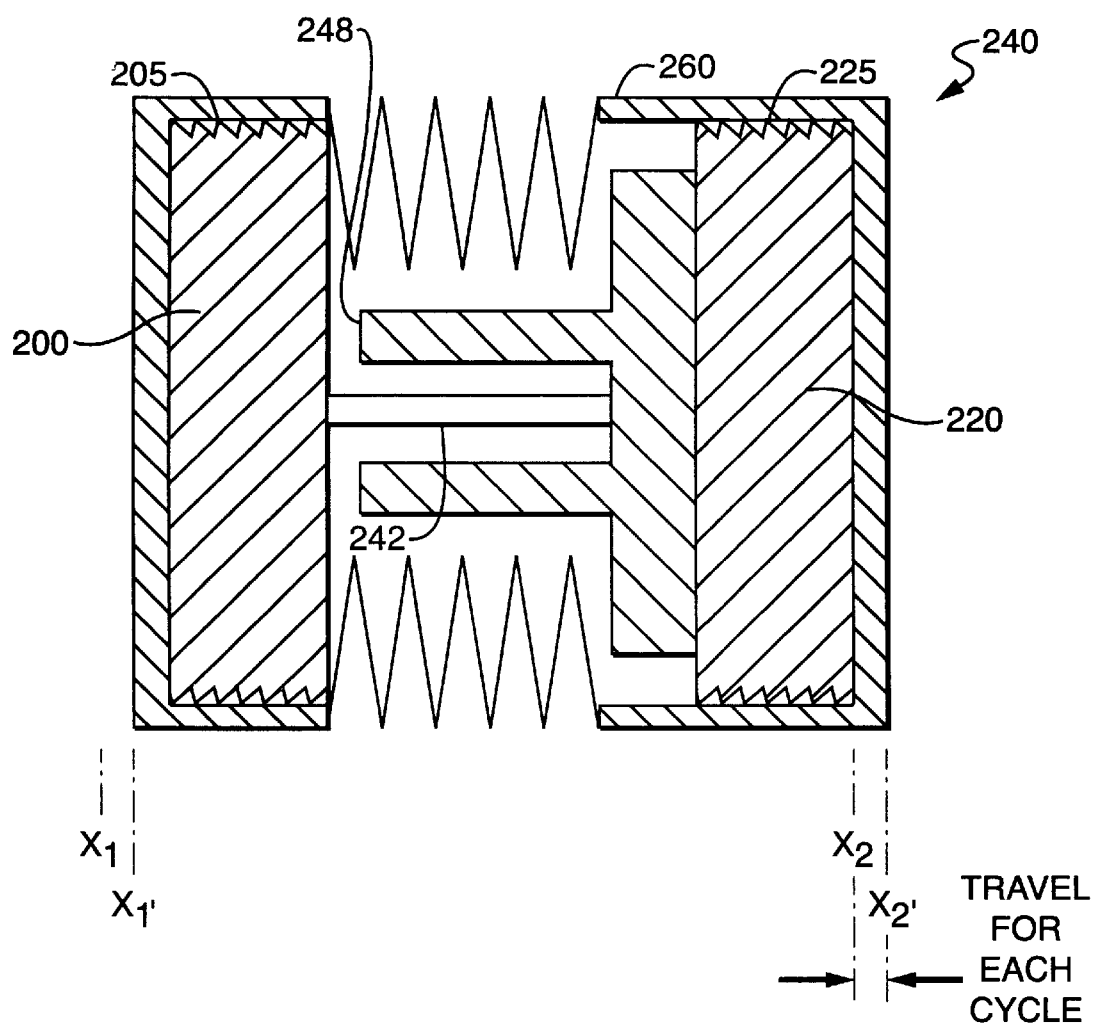

During operation of the plunger assembly 240, the shape memory element 242 is charged to pull the first lateral segment 200 longitudinally within the reservoir 230 from an initial longitudinal position x1, as illustrated in FIGS. 2a–2c, towards the second lateral segment 220 until the first lateral segment 200 is stopped by the longitudinally extending projection 248 at a second longitudinal position x1', as shown in FIGS. 2b–2c. The shape memory element 242 is adapted (e.g., sized) to be strong enough to overcome the frictional engagement between the first lateral segment 200 and the side wall of reservoir. Since the circumferential ridges 225 of the second lateral segment 220 prevent longitudinal movement of the second lateral segment 220 away from the outlet 236 of the reservoir 230, the shape memory element 242 pulls the first lateral segment 200 towards the second lateral segment 220 without moving the second lateral segment 220.

Then, the charge is removed from the two-way shape memory element 242 to push the second lateral segment 220 longitudinally within the reservoir 230 from an initial longitudinal position x2', as illustrated in FIGS. 2a–2c, away from the first lateral segment 200 to a second longitudinal position x2', as shown in FIG. 2c. Since the circumferential ridges 225 of the first lateral segment 200 prevent longitudinal movement of the first lateral segment 200 away from the outlet 236 of the reservoir 230, the expanding shape memory element 242 pushes the second lateral segment 220 longitudinally away the first lateral segment 200 without moving the first lateral segment 200.

The longitudinal difference between x2' and x2 is substantially equal to the longitudinal difference between x1' and x1, and substantially equal to the longitudinal difference between the length of the fully elongated and uncharged actuator 244 of the longitudinal segment 240 and the length of the longitudinally extending projection 248 of the longitudinal segment 240. Since both the length of the fully elongated and uncharged actuator 244 and the length of the longitudinally extending projection 248 of the longitudinal segment 240 are predetermined, the longitudinal difference between x2' and x2 is also predetermined.

The cycle of applying a charge to the shape memory element 242 of the plunger assembly 240 and then removing the charge, as illustrated in FIGS. 2a through 2c, is successively repeated (through electrical charges provided by the local processor 50) to intermittently advance the plunger assembly 240 longitudinally within the reservoir 230 and produce pulse volumes of fluid flow from the reservoir 230. Thus, the application and removal of a single charge is illustrated in FIGS. 2a through 2c, and produces a longitudinal displacement of fluid between the plunger assembly 240 and the end wall 234 of the reservoir 230 equal to the longitudinal difference between x2' and x2.

Although not shown, the processor 50 can include capacitors for storing a charge received from the power source 80 for use in providing electrical charges to the shape memory element 242 of the plunger assembly 240. The fluid delivery device 10 can be calibrated so that a single charge from the processor 50 causes the dispensing of a predetermine volume of fluid, called a pulse volume (PV), from the reservoir 30. In general, the PV is substantially equal to the longitudinal difference between x2' and x2 multiplied by the cross-sectional area of the reservoir 30.

In this manner, a desired volume to be delivered by the fluid delivery device 10 is dispensed by the application of one or more charges over a predetermined period. PV's delivered by infusion devices are typically chosen to be small relative to what would be considered a clinically significant volume. For insulin applications at a concentration of one hundred units per microliter (100 units/ml), a PV of less than two microliters, and typically a half of a microliter, is appropriate. If the fluid delivery device 10 is programmed via the remote control device 100 to deliver two units an hour, the processor 50 will deliver forty charges an hour, or a charge every ninety seconds, to the shape memory element 242. Other drugs or concentrations may permit a much larger PV. Various flow rates are achieved by adjusting the time between the cycles of charges. To give a fixed volume or bolus, multiple cycles of charges are given in rapid succession until the bolus volume is reached.

The plunger assembly 240 further includes a case 260 of resiliently flexible material enclosing the shape memory element 242 and the first and the second lateral segments 200, 220 in a fluid-tight manner. The case 260 includes a first portion 262 covering the first lateral segment 200, a second portion 264 covering the second lateral segment 220, and a collapsible bellows 266 covering the shape memory element 242 and connecting the first and the second portions 262, 264. The case 260 provides a fluid-tight seal between the outermost periphery of the second lateral segment 220 and the side wall 32 of the reservoir 30, such that fluid contained in the reservoir 30 cannot escape between the side wall 32 and the piston assembly 40 and can only exit the reservoir 30 from the outlet 36.

Figure 3:
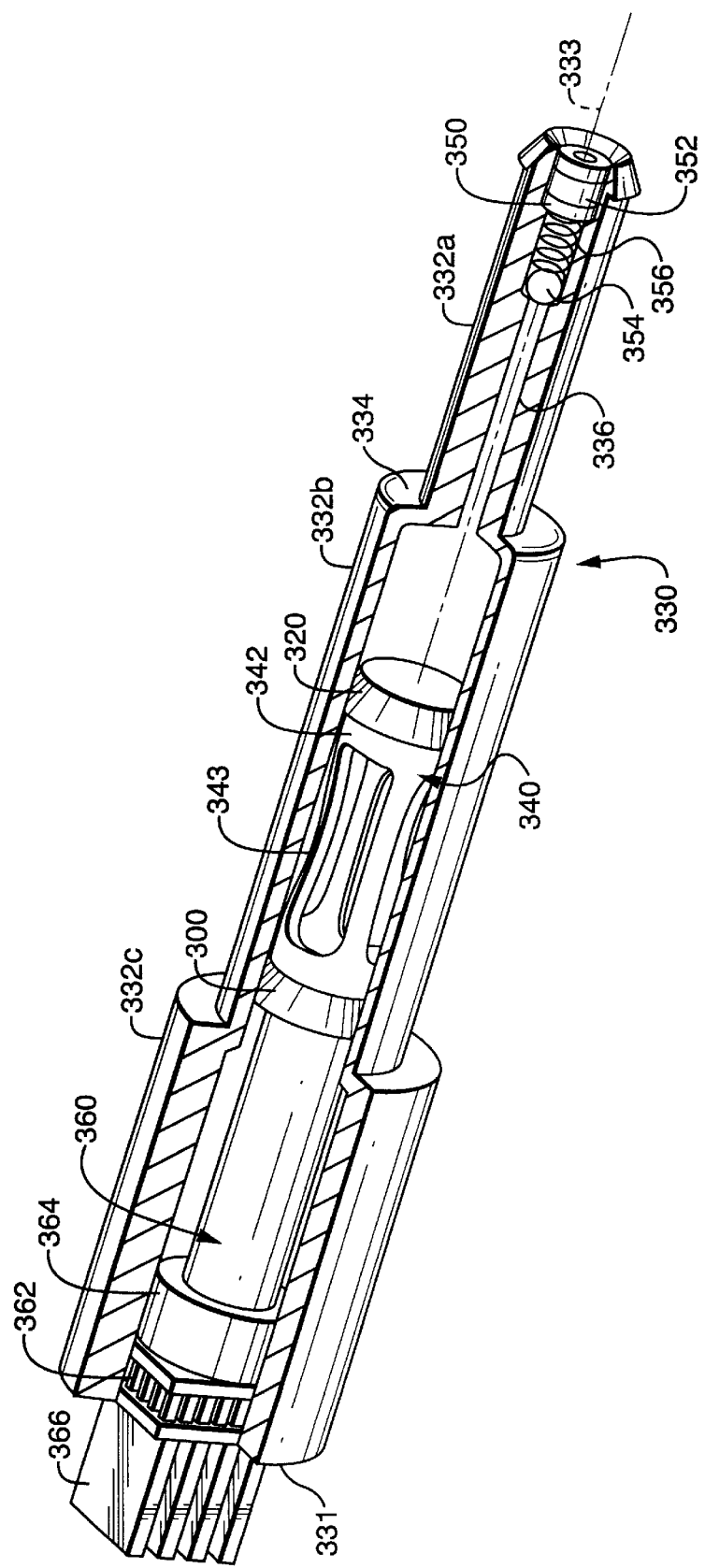
FIGS. 3 and 4 are side perspective views, partially cut-away, of another exemplary embodiment of a reservoir and a plunger assembly constructed in accordance with the present invention for use with the fluid delivery device of FIG. 1.
Figure 4:
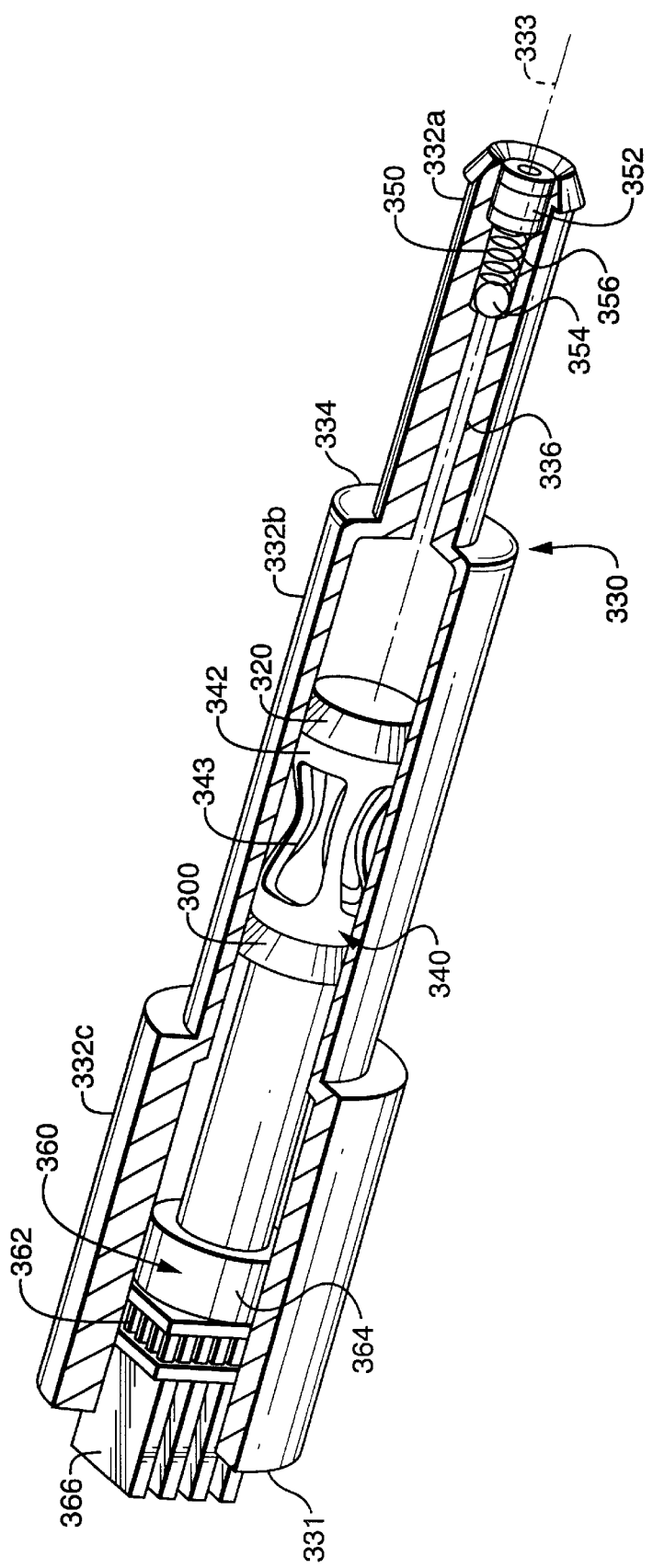

Another exemplary embodiment of a reservoir 330 and a plunger assembly 340 constructed in accordance with the present invention is shown in FIGS. 3 and 4. Elements of the reservoir 330 and the plunger assembly 340 are similar to elements of the reservoir 230 and the plunger assembly 240 of FIGS. 2 and 2a–2b such that similar elements have a similar reference numeral, but preceded by a "3" instead of a "2".

In the exemplary embodiment of the reservoir 330 of FIG. 4, the side wall 332 of the reservoir 330 includes a first section 332a extending from the outlet 336, a second section 332b extending from the first section, and a third section 332c extending from the second section. The first section 332a contains a check valve assembly 350 that prevents fluid from being drawn into the reservoir 330 through the outlet 336. The check valve assembly 350 includes a nozzle 352, a ball valve 354, and a spring 356 biasing the ball valve from the nozzle. The second section 332b of the side wall has a larger cross-section than the first section 332a of the side wall, and the third section 332c of the side wall has a larger cross-section than the second section 332b of the side wall.

The plunger assembly 340 is received in the second section 332b of the side wall 332 of the reservoir 330 and includes a shape memory element 342 comprising an elongated tube extending parallel with the longitudinal axis 333 of the reservoir 330 between first and second lateral elements 300, 320 of the plunger assembly 340. In the exemplary embodiment shown, the shape memory element 342 and the first and the second lateral elements 300, 320 are formed from a unitary piece of shape memory material. Preferably, the tubular shape memory element 342 has a generally hourglass shape and includes elongated cut-outs 343 extending parallel with the longitudinal axis 333 of the reservoir 330. The elongated cut-outs 343 reduce the amount of material that comprises the tubular shape memory element 342 and therefore increase the response time of the shape memory element 342 upon a charge being applied or removed from the shape memory element 342 (i.e., the same tubular element without the elongated cut-outs does not heat and contract upon being charged as fast as the same tubular element with the elongated cut-outs).

Figure 5:
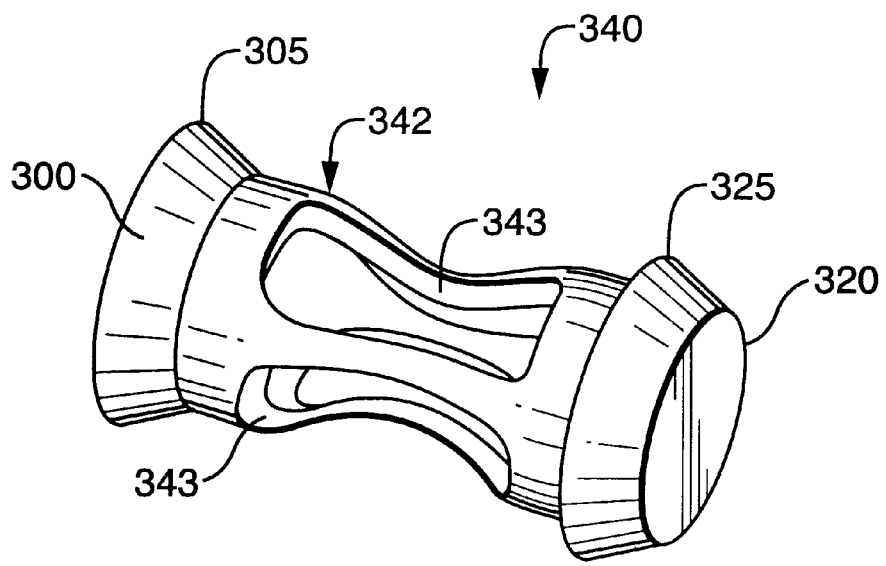
FIGS. 5 and 6 are further enlarged side perspective views illustrating operation of the plunger assembly of FIGS. 3 and 4.
Figure 6:
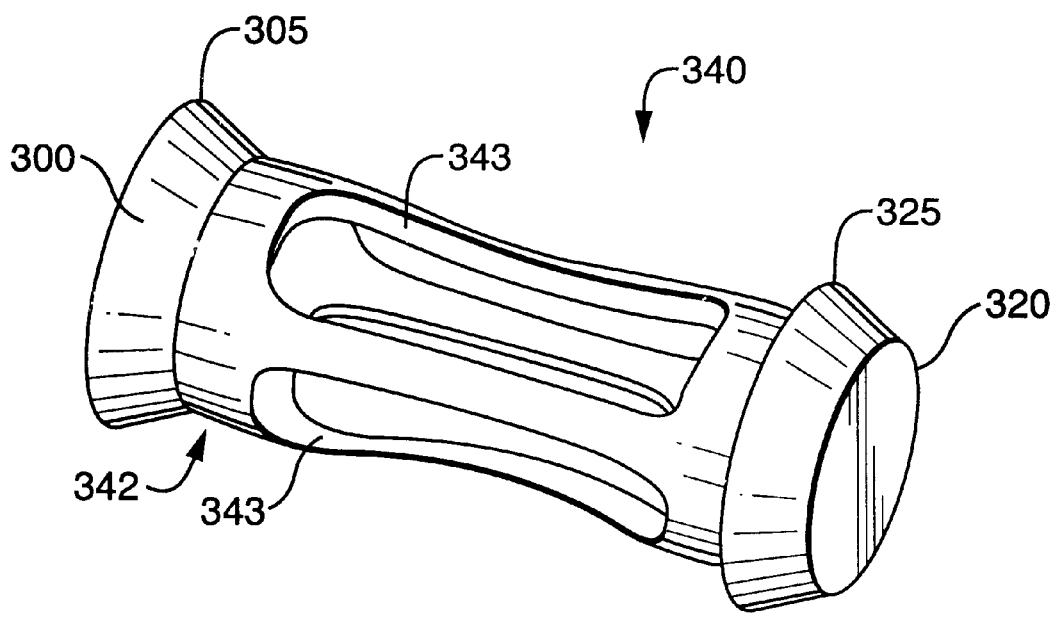

As also shown in FIGS. 5 and 6, the first and the second lateral segments 300, 320 are each sized and shaped to frictionally engage the side wall 332 of the reservoir 330, to allow longitudinal movement of the lateral segments 300, 320 towards the outlet 336 of the reservoir, and substantially prevent longitudinal movement of the lateral segments 300, 320 away from the outlet 336 of the reservoir. For example, the lateral segments 300, 320 respectively include outer peripheries 305, 325 which slope radially inwardly toward the outlet 336 of the reservoir 330. The frictional engagement force of the lateral segments 300, 320 against the side wall 332 are designed to be slightly less than the force generated by the shape memory element 342 upon changing length.

If desired, the plunger assembly 340 can include a rigid, longitudinally extending projection (similar to the rigid, longitudinally extending projection 248 of FIGS. 2 and 2a–2c) for limiting the smallest longitudinal distance that can be attained between the first and the second lateral segments 300, 320 upon actuation of the shape memory element 342.

During operation of the plunger assembly 340, the shape memory element 342 is charged to pull the first lateral segment 300 longitudinally within the reservoir 330 towards the second lateral segment 320, as shown in FIGS. 3 and 4. FIG. 3 shows the plunger assembly 340 in an uncharged state while FIG. 4 shows the plunger assembly 340 in a charged state. The outer circumferential ring 325 of the second lateral segment 320 prevents longitudinal movement of the first lateral segment 300 away from the outlet 336 of the reservoir 330, so that the contracting shape memory element 342 pulls the first lateral segment 300 longitudinally towards the second lateral segment 320 without moving the second lateral segment 320.

Then, the charge is removed from the two-way shape memory element 342 to push the second lateral segment 320 longitudinally within the reservoir 330 away from the first lateral segment 200. The sized and shaped outer periphery of 305 of the first lateral segment 300 prevents longitudinal movement of the first lateral segment 300 away from the outlet 336 of the reservoir 330, so that the expanding shape memory element 342 pushes the second lateral segment 320 longitudinally away the first lateral segment 300 without moving the first lateral segment 300. The cycle of applying a charge to the shape memory element 342 of the plunger assembly 340 and then removing the charge, as illustrated respectively in FIGS. 5 and 6, is successively repeated (through electrical charges provided by the local processor 50) to intermittently advance the plunger assembly 340 longitudinally within the reservoir 330 and produce pulse volumes of fluid flow from the reservoir 330.

As shown in FIGS. 3 and 4, the plunger assembly 340 can be provided with a cooler assembly 360 in contact with the shape memory element 342. The cooler assembly 360 dissipates heat from, and speeds cooling of, the shape memory element 342 to improve the response time of the shape memory element 342 upon an electric charge being removed from the shape memory element 342. In the exemplary embodiment shown, the cooler assembly 360 includes a thermoelectric cooler 362 thermally in contact with the shape memory element 342 through a thermal conduit 364, and a heat sink 366 thermally in contact with the thermoelectric cooler 362. The cooler assembly 360 is slidably received in the third section 332c of the side wall of the reservoir 330 and moves longitudinally with the plunger assembly 340.

An additional exemplary embodiment of a plunger assembly 440 constructed in accordance with the present invention is shown in FIGS. 7 through 12. The plunger assembly 440 of FIGS. 7 through 12 is similar to the plunger assembly 340 of FIGS. 3 through 6 such that similar element have the same reference numeral, but preceded by a "4" instead of a "3".

The plunger assembly 440 includes a shape memory element 442 comprising an elongated tube extending parallel with the longitudinal axis 333 of the reservoir 330 between first and second lateral elements 400, 420 of the plunger assembly. In the exemplary embodiment shown the tubular shape memory element 442 is provided in the form of a collapsible bellows and is formed from a unitary piece of shape memory material with the first and the second lateral elements 400, 420.

Figure 10:
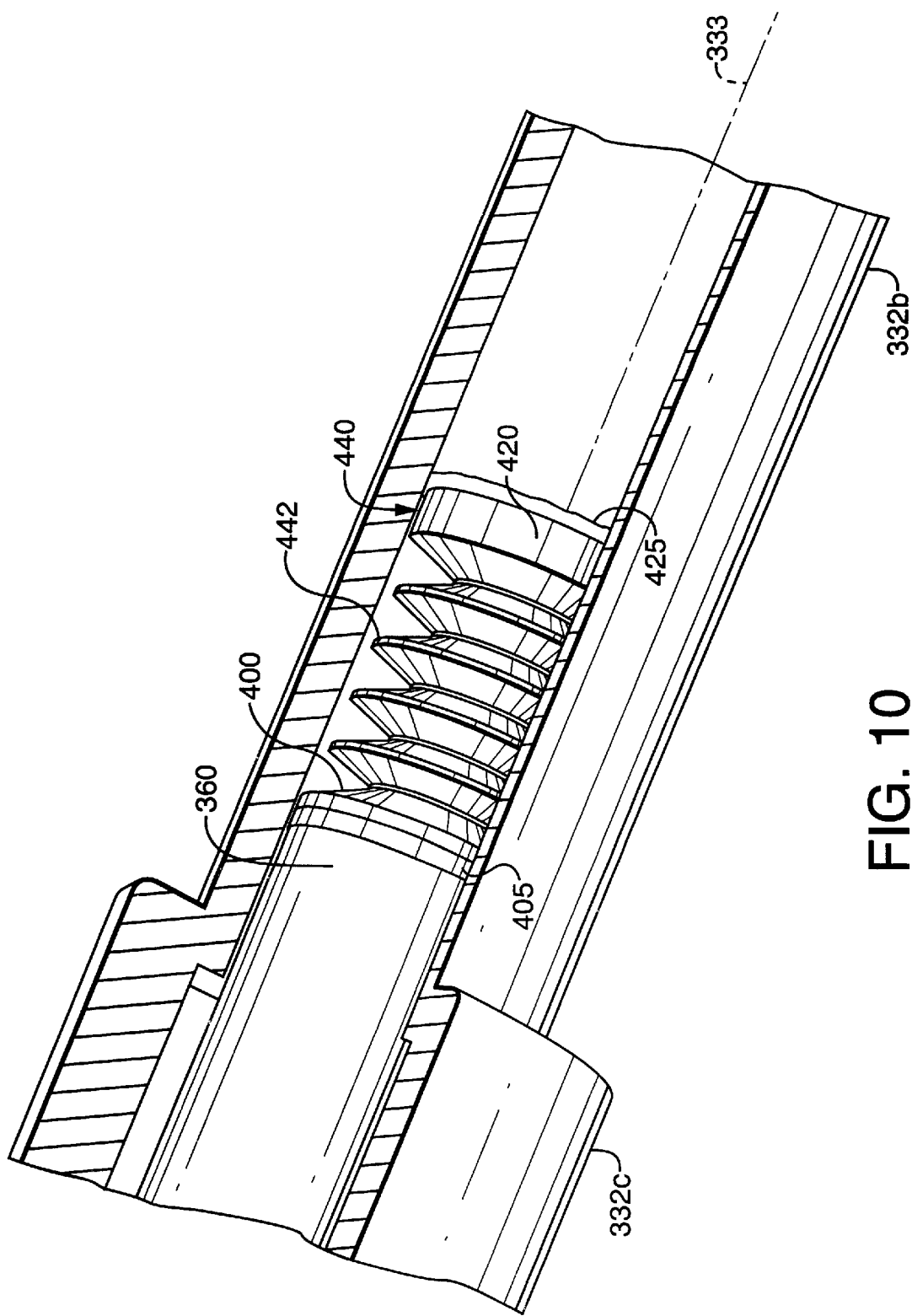
FIG. 10 is a further enlarged side perspective view, partially cut-away, of a portion of the reservoir and the plunger assembly of FIG. 9.
Figure 11:
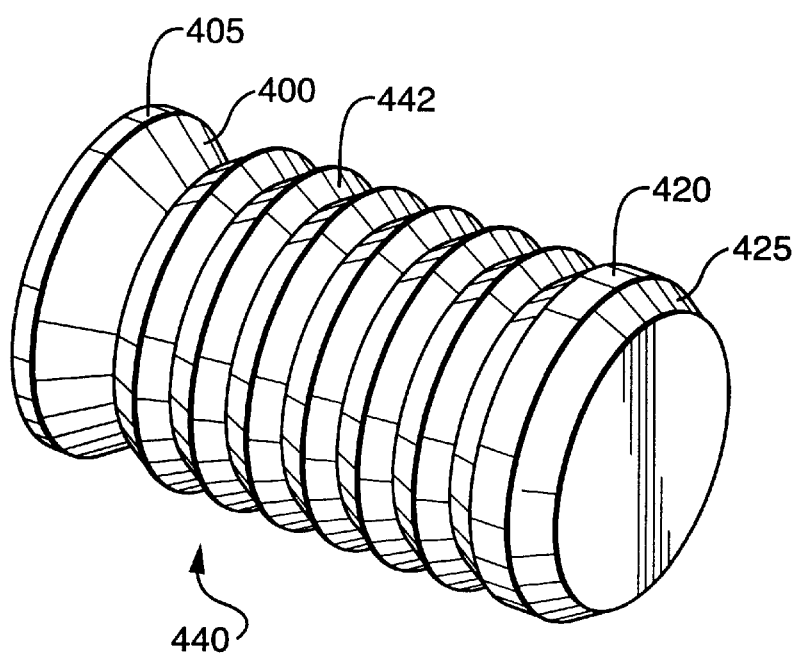
FIGS. 11 and 12 are further enlarged side perspective views illustrating operation of the plunger assembly of FIGS. 7 through 9, and wherein the plunger assembly is partially cut-away in FIG. 12.
Figure 12:
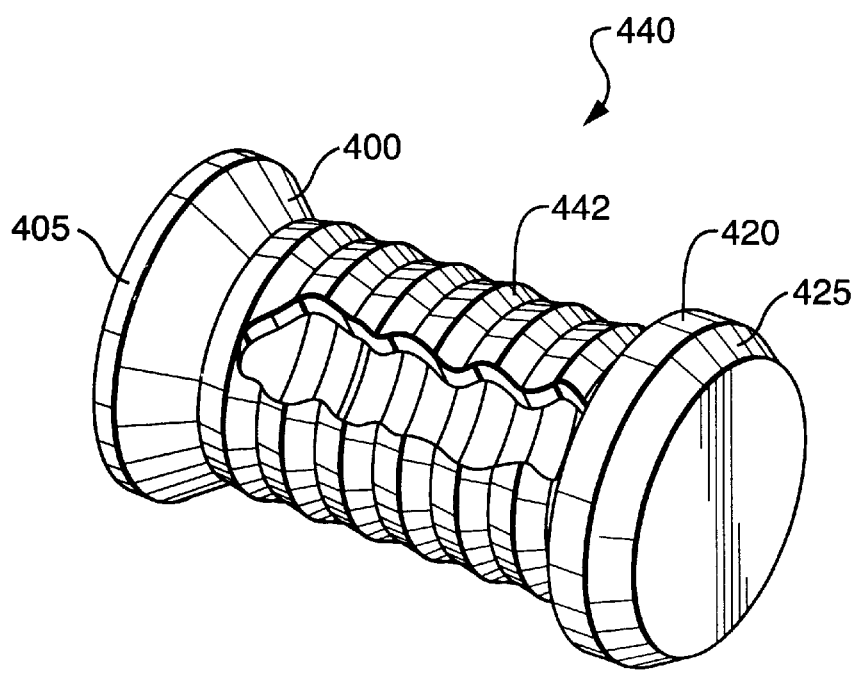

As shown best in FIGS. 10 through 12, the first and the second lateral segments 400, 420 each respectively includes an outer circumferential ring 405, 425 sized and shaped to frictionally engage the side wall 332 of the reservoir 330, allow longitudinal movement of the lateral segments 400, 420 towards the outlet 336 of the reservoir, and substantially prevent longitudinal movement of the lateral segments 400, 420 away from the outlet 336 of the reservoir. If desired, the plunger assembly 440 can include a rigid, longitudinally extending projection (similar to the rigid, longitudinally extending projection 248 of FIGS. 2 and 2a–2c) for limiting the smallest longitudinal distance that can be attained between the first and the second lateral segments 400, 420 upon actuation of the shape memory element 442.

Figure 7:
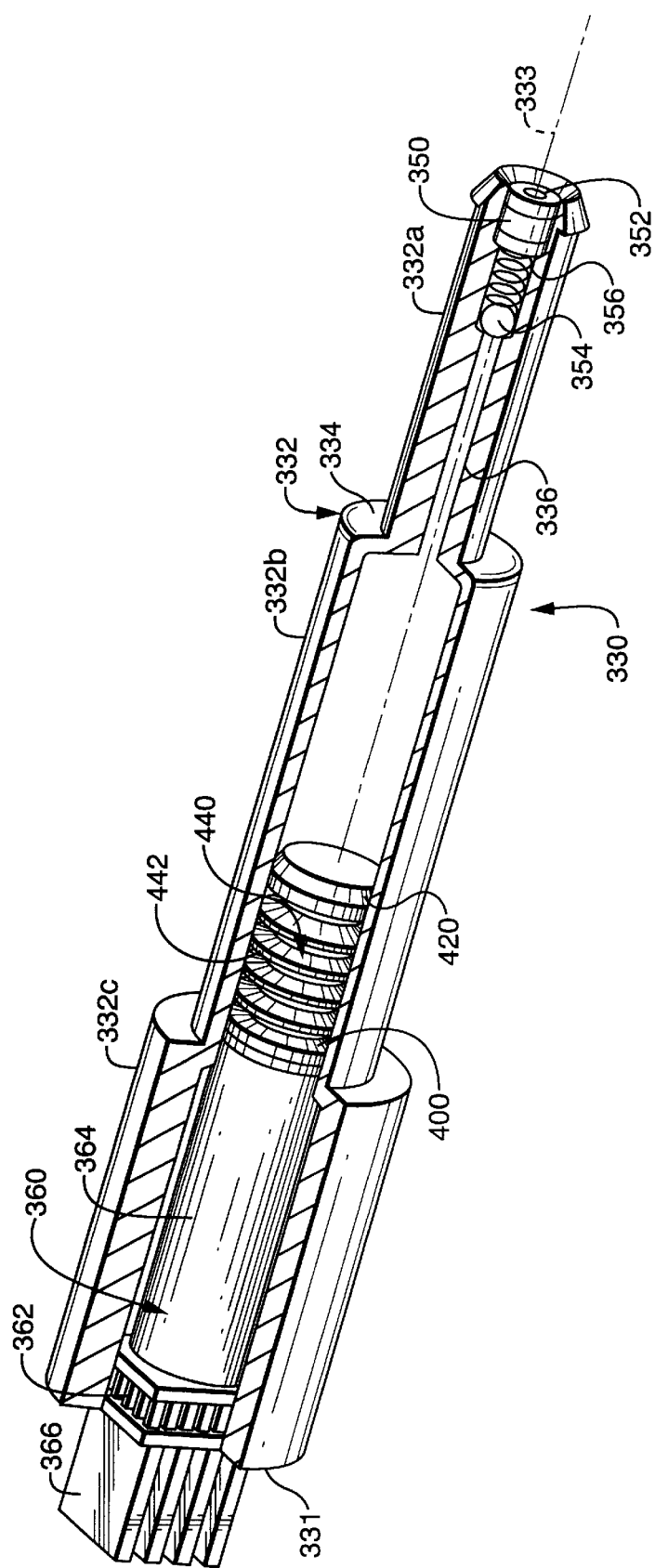
FIGS. 7 through 9 are side perspective views, partially cut-away, of an additional exemplary embodiment of a reservoir and a plunger assembly constructed in accordance with the present invention for use with the fluid delivery device of FIG. 1.
Figure 8:
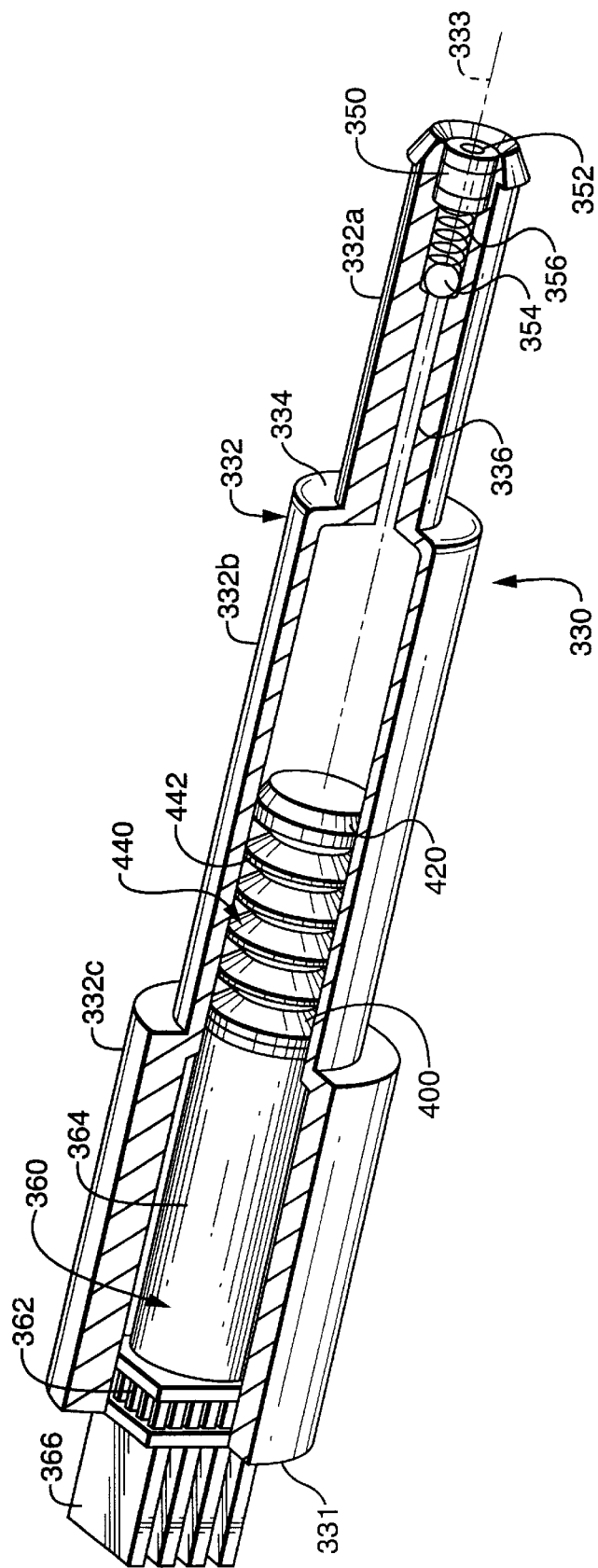
Figure 9:
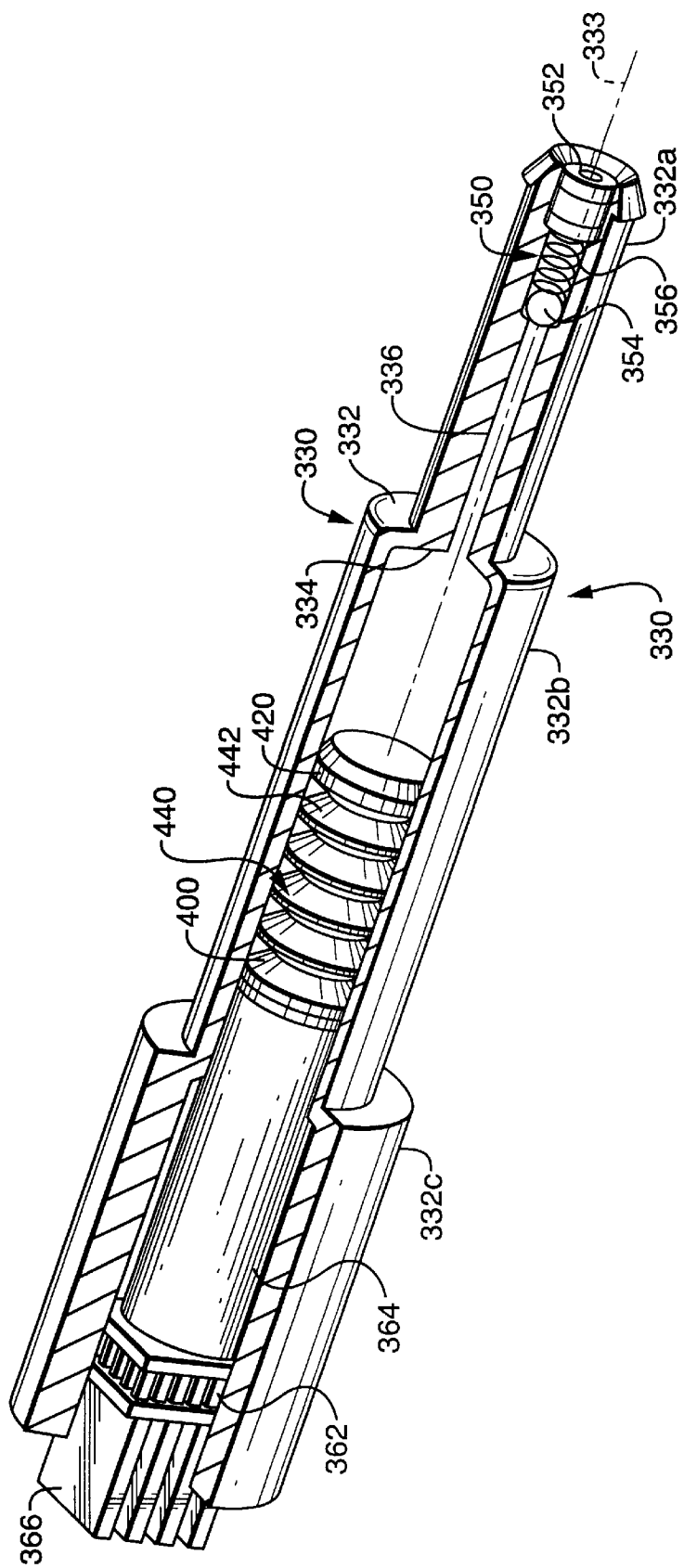

During operation of the plunger assembly 440, the shape memory element 442 is charged to pull the first lateral segment 400 longitudinally within the reservoir 330 towards the second lateral segment 420, as shown in FIG. 7. FIG. 7 shows the plunger assembly 440 in a charged state, while FIG. 8 shows the plunger assembly 440 in an uncharged state and FIG. 9 shows the plunger assembly 440 in a charged state. The outer circumferential ling 425 of the second lateral segment 420 prevents longitudinal movement of the first lateral segment 400 away from the outlet 336 of the reservoir 330, so that the contracting shape memory element 442 pulls the first lateral segment 400 longitudinally towards the second lateral segment 420 without moving the second lateral segment 420, as shown in FIGS. 7 and 9.

Then, the charge is removed from the two-way shape memory element 442 to push the second lateral segment 420 longitudinally within the reservoir 430 away from the first lateral segment 400, as shown in FIG. 8. The outer circumferential ring 405 of the first lateral segment 400 prevents longitudinal movement of the first lateral segment 400 away from the outlet 336 of the reservoir 330, so that the expanding shape memory element 442 pushes the second lateral segment 420 longitudinally away the first lateral segment 400 without moving the first lateral segment 400. The cycle of applying a charge to the shape memory element 442 of the plunger assembly 440 and then removing the charge, as illustrated respectively in FIGS. 11 and 12, is successively repeated (through electrical charges provided by the local processor 50) to intermittently advance the plunger assembly 440 longitudinally within the reservoir 330 and produce pulse volumes of fluid flow from the reservoir 330.

As illustrated by the above described exemplary embodiments, the present invention generally provides a device 10 for delivering fluid, such as insulin for example, to a patient. The device 10 includes an exit port assembly 70, and a reservoir 230 including an outlet 236 connected to the exit port assembly 70 and a side wall 232 extending along a longitudinal axis 233 towards the outlet 236. A plunger assembly (e.g., 240, 340, 440) is received in the reservoir 230 and is movable along the longitudinal axis 233 of the reservoir 230 towards the outlet 236 of the reservoir in order to cause fluid to be dispensed from the reservoir to the exit port assembly 70. The plunger assembly (e.g., 240, 340, 440) of the present invention utilizes a two-way shape memory element (e.g., 242, 342, 442)

Figure 17:
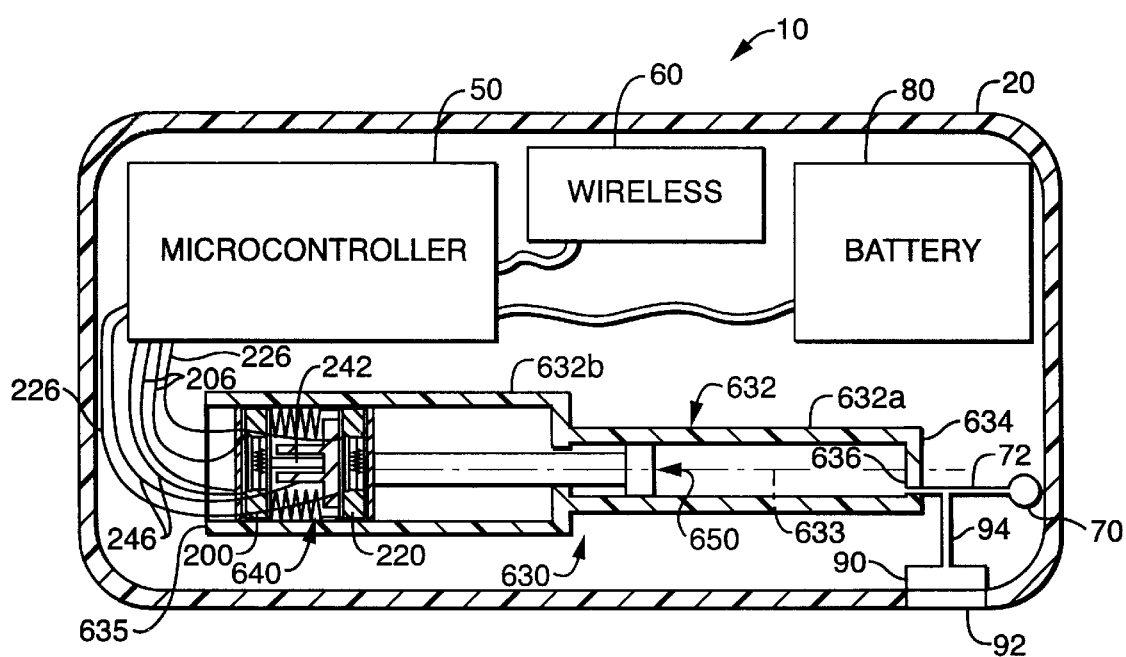
FIG. 17 is a sectional side view of a fluid delivery device similar to the fluid delivery device of FIG. 2 showing another exemplary embodiment of a reservoir and a plunger assembly constructed in accordance with the present invention for causing fluid to be dispensed from the device.

FIG. 17 shows a fluid delivery device similar to the fluid delivery device of FIG. 2, but including another exemplary embodiment of a reservoir 630 and a plunger assembly 640 constructed in accordance with the present invention for causing fluid to be dispensed from the device. The reservoir 630 and the plunger assembly 640 are similar to the reservoir and the plunger assembly of FIG. 2 such that similar elements have the same reference numerals.

The reservoir 630 is provided with a side wall 632 extending along a longitudinal axis 633 between an open end 635 and an end wall 634 of the reservoir. The end wall 634 includes an outlet, or an opening 636 that functions as an outlet and an inlet. The side wall 632 includes a first section 632a extending from the outlet 636, and a second section 632b extending from the first section 632a to the open end 635 (it should be noted that the reservoirs disclosed herein can be provided with closed ends if desired).

The plunger assembly 640 is received in the second section 632b of the side wall 632 of the reservoir 630. The plunger assembly 640 includes a strut 650 extending along the longitudinal axis 633 of the reservoir 630 and received in the first section 632a of the side wall 632 of the reservoir 630. The strut 650 is shaped and sized such that a fluid-tight seal is generally formed between the strut 650 and the first section 632a of the side wall 632 of the reservoir 630 so that movement of the plunger assembly 640 and the strut 650 towards the end wall 634 of the reservoir 630 forces fluid located between the strut 650 and the end wall 634 through the outlet 636 to the exit port assembly 70.

Features and advantages of the exemplary embodiments of the reservoir 630 and the plunger assembly 640 of FIG. 17 include, but are not limited to, allowing the lateral segments 200, 220 of the plunger assembly 640 to have a cross-sectional dimensions that are different than the cross-sectional dimension of the strut 650, such that a desired pulse volume (PV) produced by the reservoir 630 and the plunger assembly 640 can be further refined. In the exemplary embodiment of FIG. 17, the lateral segments 200, 220 of the plunger assembly 640 are provided with cross-sectional dimensions that are larger than the cross-sectional dimension of the strut 650 (i.e., the first section 632a of the side wall 632 of the reservoir 630 has a cross-sectional dimension that is smaller than a cross-sectional dimension of the second section 632b of the side wall 632). However, the lateral segments 200, 220 of the plunger assembly 640 can be provided with cross-sectional dimensions that are smaller than the cross-sectional dimension of the strut 650 (i.e., the first section 632a of the side wall 632 of the reservoir 630 can be provided with a cross-sectional dimension that is larger than a cross-sectional dimension of the second section 632b of the side wall 632) if desired.

Figure 13:
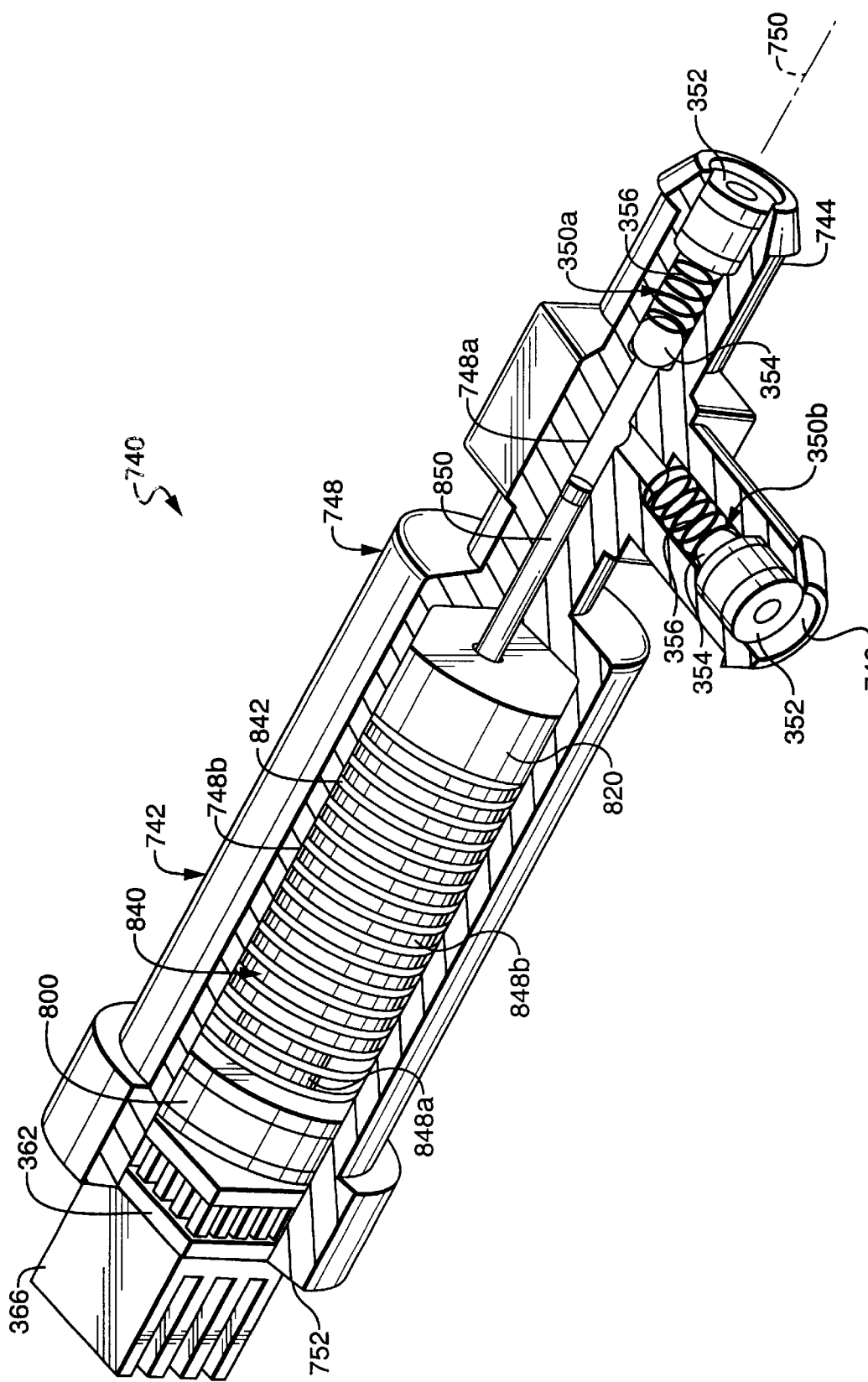
FIGS. 13 and 14 are side perspective views, partially cut-away, of a fluid dispenser constructed in accordance with the present invention for use with the fluid delivery device of FIG. 1.
Figure 14:
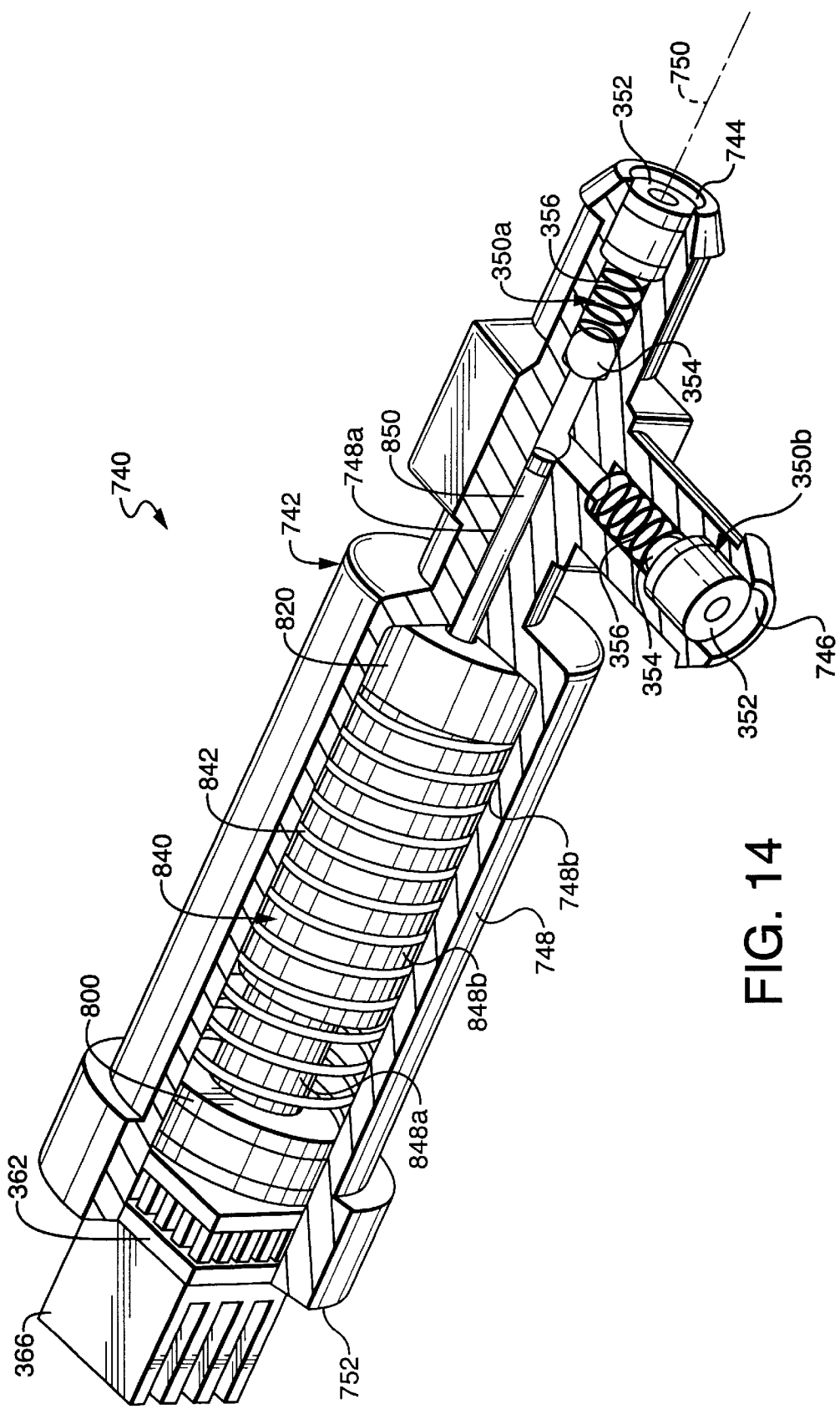

Referring now to FIGS. 13 and 14, there is shown an exemplary embodiment of a dispenser 740 constructed in accordance with the present invention for use as part of the fluid delivery device 10 of FIG. 1. In general, the dispenser 740 is connected to a separate reservoir (not shown) within the fluid delivery device 10 and operates as a pump to cause fluid flow from the reservoir to the exit port assembly of the device 10. The dispenser 740 is controlled by the local processor of the device, similar to the plunger assembly 240 of FIG. 2.

The dispenser 740 includes a container 742 having an outlet 744 for connection to the exit port assembly of the fluid delivery device 10, an inlet 746 for connection to a reservoir of the device 10, and a side wall 748 extending along a longitudinal axis 750 away from the outlet 744 and the inlet 746 to an open end 752. A check valve assembly 350a is positioned in the outlet 744 and prevents fluid from being drawn into the container 742 through the outlet 744. The check valve assembly 350a includes a nozzle 352, a ball valve 354, and a spring 356 biasing the ball valve away from the nozzle 352. A check valve assembly 350b is also positioned in the inlet 746 and prevents fluid from being pushed out of the container 742 through the inlet 746. The check valve assembly 350b includes a nozzle 352, a ball valve 354, and a spring 356 biasing the ball valve 354 to the nozzle 352.

The dispenser 740 also includes a plunger assembly 840 received in the container 742 and including a first lateral segment 800 extending laterally with respect to the longitudinal axis 750 of the container 742 and contacting the side wall 748 of the container, and a second lateral segment 820 positioned between the first lateral segment 800 and the inlet 746 and the outlet 744 of the container 742 and longitudinally spaced from the first lateral segment 800. The second lateral segment 820 also extends laterally with respect to the longitudinal axis 750 of the container and contacts the side wall 748 of the container 742. The first lateral segment 800 is fixed in position with respect to the side wall 748 of the container 742, and the second lateral segment 820 is sized and shaped to slide within the side wall 748 of the container 742.

A shape memory element 842 connects the first and the second lateral segments 800, 820 and has a changeable length decreasing from an uncharged length to a charged length when at least one charge is applied to the shape memory element 842. The shape memory element of the embodiment of FIGS. 13 and 14 comprises an elongated, two-way shape memory material, provided in the shape of a coiled spring 842. The elongated shape memory element 842 is secured between the first and the second lateral segments 800, 820 of the plunger assembly 840 and extends generally parallel to the axis 750 of the container 742. Although not shown, the fluid delivery device 10 includes wires for connecting opposite ends of the shape memory element 842 to the processor of the fluid delivery device 10 of FIG. 1, such that the processor can apply electrical charges to the shape memory element 842.

When a charge is applied to the elongated shape memory element 842, the length of the shape memory element 842 decreases from an uncharged length to a charged length. The shape memory element 842 is arranged such that the changeable length of the shape memory element decreasing from an uncharged length to a charged length causes the second lateral segment 820 to be drawn towards the first lateral segment 800 and away from the inlet 746 of the container 742, as shown in FIG. 13, such that fluid is drawn into the container 742 against the one-way valve assembly 350b of the inlet 746. When the charge is removed from the elongated shape memory element 842, the length of the shape memory element increases from the charged length to the uncharged length and causes the second lateral segment 820 to be biased away from the first lateral segment 800 and towards the outlet 744 of the container 742, as shown in FIG. 14, such that fluid is pushed out of the container 742 against the one-way valve assembly 350a of the outlet 744.

In this manner, the dispenser 740 acts as a pump when charges are successively applied to the two-way shape memory element 842 so that fluid is moved from the reservoir of the fluid delivery device, through the dispenser 740, and to the outlet port assembly of the fluid delivery device.

As an alternative to the two-way shape memory element 842, the plunger assembly 840 can be provided with a spring biasing the first and the second lateral segments 800, 820 longitudinally apart, and an actuator arranged to overcome the spring and bias the first and the second lateral segments 800, 820 longitudinally together upon actuation. A similar arrangement is disclosed in co-pending U.S. patent application Ser. No. 10/163,188, which was filed on the same day as the present application, is also entitled PLUNGER ASSEMBLY FOR PATIENT INFUSION DEVICE, and is assigned to the assignee of the present application and incorporated herein by reference. The actuator can comprise one or more one-way shape memory elements, piezoelectric elements, or solenoids for example.

The plunger assembly 840 also includes at least one rigid, longitudinally extending projection 848 that limits the smallest longitudinal distance that can be attained between the first and the second lateral segments 800, 820 upon actuation of the shape memory element 842 (i.e., when the first and the second lateral segments are pulled together by the charged shape memory element). In the exemplary embodiment shown, the plunger assembly 840 includes two longitudinally extending projections 848a, 848b, one extending from the first lateral segment 800 and one extending from the second lateral segment 820. One longitudinally extending projection 848a is received axially within the other longitudinally extending projection 848a, such that the two longitudinally extending projections 848a, 848b also act to guide movement of the second lateral segment 820 away from and towards the first lateral segment 800.

In the exemplary embodiment shown, the side wall 748 of the container 742 includes a first section 748a extending from the inlet 746 and the outlet 744, and a second section 748b extending from the first section 748a to the open end 752 of the container 742 (it should be noted that the container disclosed herein can be provided with a closed end if desired). The plunger assembly 840 is received in the second section 748b of the side wall 748 of the container 742 and includes a strut 850 extending along the longitudinal axis 750 of the container 742 and received in the first section 748a of the side wall 748 of the container 742. The strut 850 is shaped and sized such that a fluid-tight seal is generally formed between the strut 850 and the first section 748a of the side wall 748 of the container 742 so that the strut 850 and the first section 748a form a pump chamber.

Figure 15:
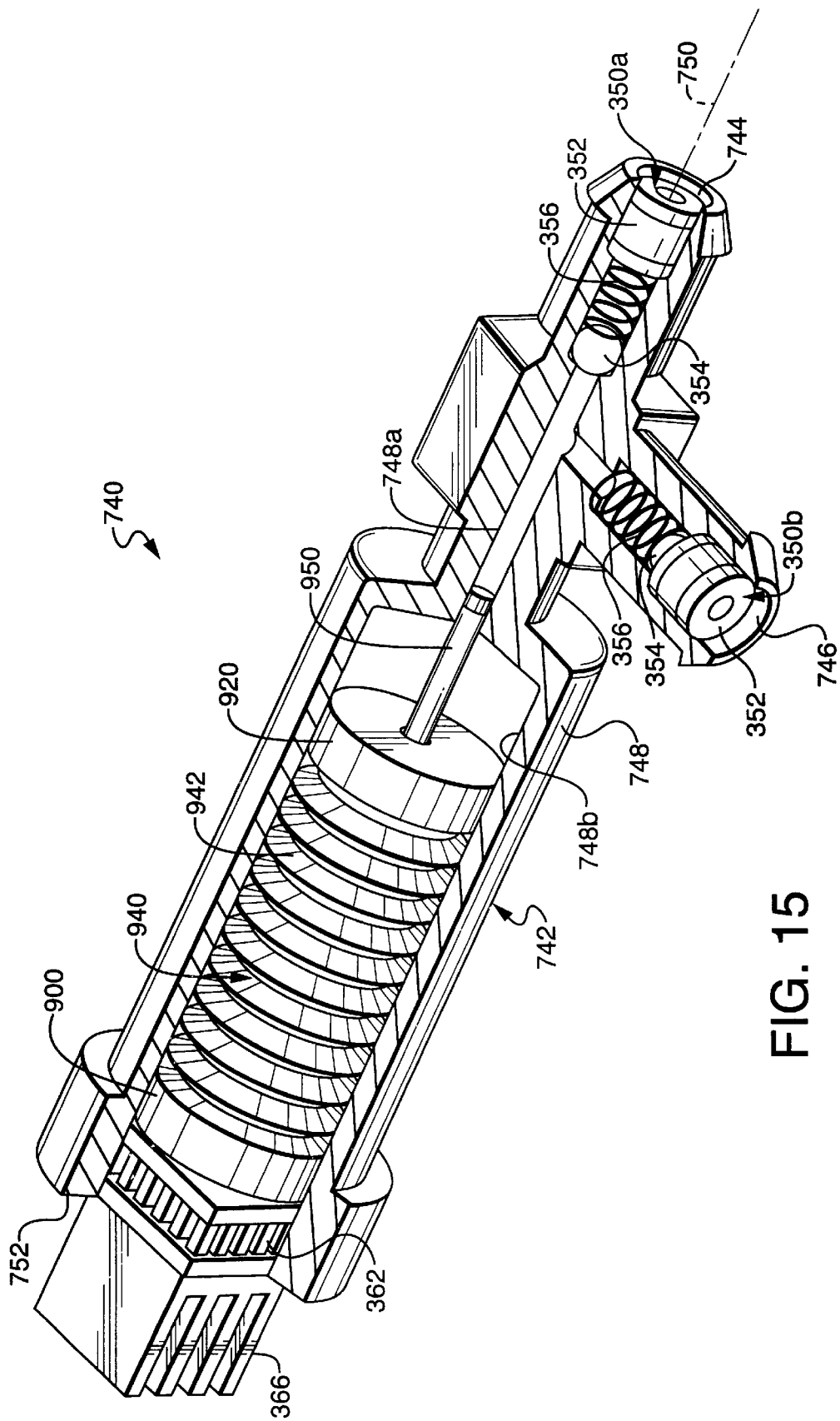
FIGS. 15 and 16 are side perspective views, partially cut-away, of a fluid dispenser constructed in accordance with the present invention for use with the fluid delivery device of FIG. 1.
Figure 16:
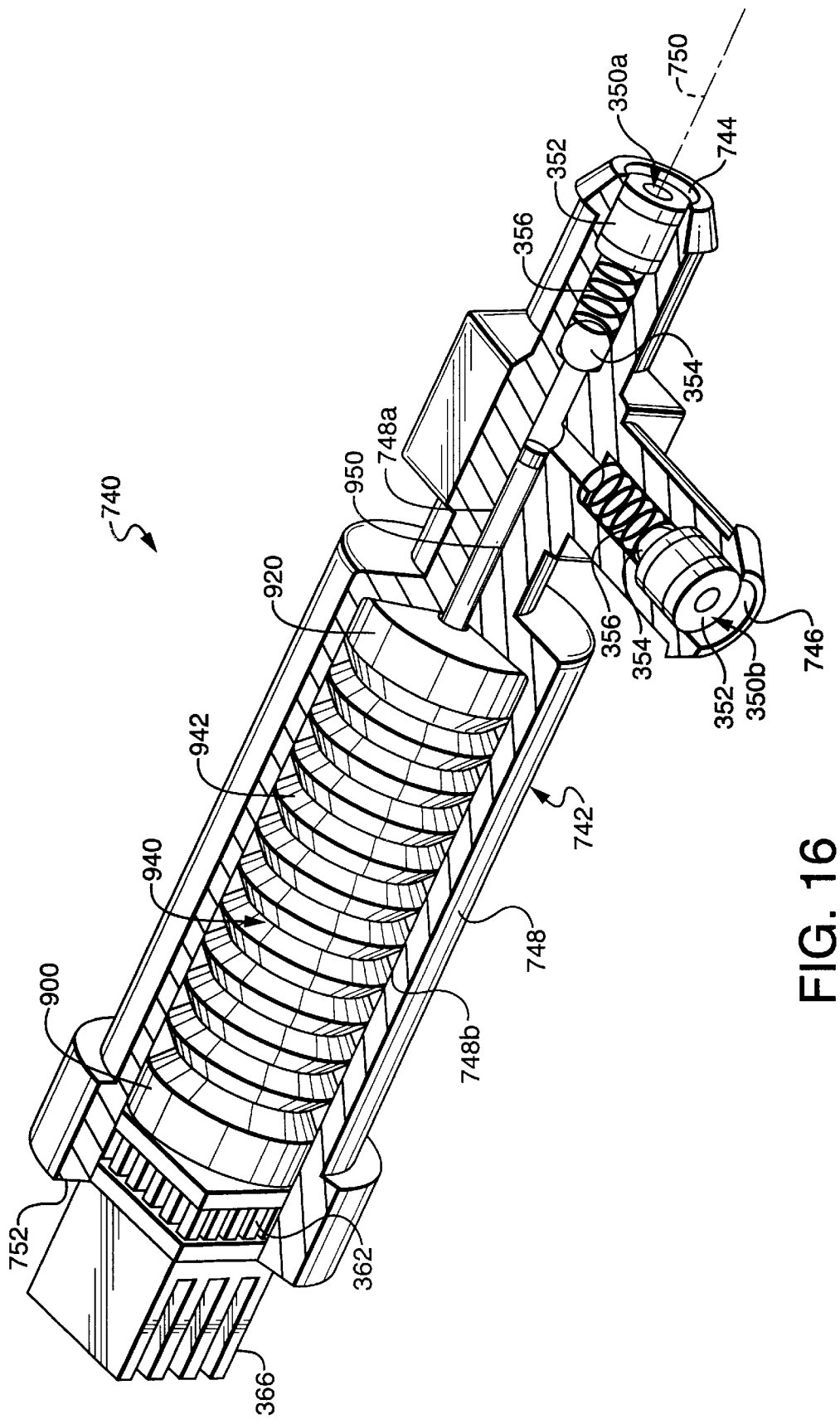

An additional exemplary embodiment of a dispenser 740a constructed in accordance with the present invention is shown in FIGS. 15 and 16. The dispenser 740a of FIGS. 15 and 16 is similar to the dispenser 740 of FIGS. 13 and 14 such that similar elements have the same reference numerals. A plunger assembly 940 of the dispenser 740a includes a shape memory element comprising an elongated, tubular, collapsible bellows 942 extending between first and second lateral segments 900, 920. The plunger assembly 940 also includes a strut 950 extending from the second lateral segment 920 into the first section 748a of the container 742.

In any event, it should be understood that the embodiments described herein are merely exemplary and that a person skilled in the art may make variations and modifications to the embodiments described without departing from the spirit and scope of the present invention. For example, some linear actuators have a limited contraction distances (i.e., small change in length). A shape memory element for example may be only able to contract approximately 5% of its length upon being charged. In applications where this small change in length is insufficient, various geometric design alternatives can be used to create sufficient linear motion based on the small change in length of the shape memory element. The simplest geometric design alternative, for example, may be to use a longer shape memory element connected back and forth multiple times between the two objects to be pulled together. Alternatively, the shape memory element can be attached to a shorter arm of a lever (or other length versus force exchange mechanism), utilizing the large forces generated by the shape memory element to "exchange" force for increased travel. In any event, all such equivalent variations and modifications are intended to be included within the scope of this invention as defined by the appended claims.

What is claimed is:

1. A device for delivering fluid to a patient, comprising:
   an exit port assembly;
   a reservoir including an outlet connected to the exit port assembly, and a side wall extending along a longitudinal axis towards the outlet; and
   a plunger assembly received in the reservoir and movable along the longitudinal axis of the reservoir towards the outlet of the reservoir, the plunger assembly including,
      a first lateral segment extending laterally with respect to the longitudinal axis of the reservoir and contacting the side wall of the reservoir,
      a second lateral segment positioned between the first lateral segment and the outlet of the reservoir, the second lateral segment extending laterally with respect to the longitudinal axis of the reservoir and contacting the side wall of the reservoir, and longitudinally spaced from the first lateral segment, and
      a shape memory element having a changeable length decreasing from an uncharged length to a charged length when at least one charge is applied to the shape memory element, connecting the first and the second lateral segments, and comprising two-way shape memory material.

2. A device according to claim 1, wherein the shape memory element is elongated and extends between a first end connected to the first lateral segment and a second end connected to the second lateral segment.

3. A device according to claim 2, wherein the shape memory element comprises a wire having a generally circular cross-section.

4. A device according to claim 1, wherein the first and the second lateral segments include outer circumferential rings shaped and oriented to engage the side wall of the reservoir and substantially prevent movement of the first and the second lateral segments away from the outlet of the reservoir.

5. A device according to claim 1, wherein the shape memory element is made of a nickel and titanium alloy.

6. A device according to claim 1, wherein the plunger assembly further includes a rigid projection positioned between the first and the second lateral segments and extending parallel with the longitudinal axis of the reservoir for limiting the closeness of the first and the second lateral segments.

7. A device according to claim 6, wherein the rigid projection of the plunger assembly has a substantially predetermined length extending parallel with the longitudinal axis of the reservoir.

8. A device according to claim 7, wherein the shape memory element has a substantially predetermined uncharged length.

9. A device according to claim 1, wherein the shape memory element has a substantially predetermined uncharged length and a substantially predetermine charged length.

10. A device according to claim 1, wherein the plunger assembly further includes a case of resiliently flexible material enclosing the shape memory element and the first and the second lateral segments in a fluid-tight manner.

11. A device according to claim 10, wherein the case of the plunger assembly includes a first portion covering the first lateral segment, a second portion covering the second lateral segment, and a collapsible bellows covering the shape memory element and connecting the first and the second portions.

12. A device according to claim 1, wherein the first and the second lateral segments are substantially prevented from moving away from the outlet of the reservoir.

13. A device according to claim 1, further comprising:
    a local processor electrically connected to the shape memory element of the plunger assembly and programmed to provide electrical charges to the shape memory element based upon flow instructions;
    a wireless receiver connected to the local processor for receiving flow instructions from a separate, remote control device and delivering the flow instructions to the local processor; and
    a housing containing the reservoir, the exit port assembly, the plunger assembly, the local processor and the wireless receiver, and wherein the housing is free of user input components for providing flow instructions to the local processor.

14. A system including a fluid delivery device according to claim 13, and further comprising a remote control device separate from the fluid delivery device and including:
    a remote processor;
    user interface components connected to the remote processor for allowing a user to provide flow instructions to the remote processor; and
    a transmitter connected to the remote processor for transmitting the flow instructions to the receiver of the fluid delivery device.

15. A device according to claim 1, wherein the reservoir contains a therapeutic fluid.

16. A device according to claim 15, wherein the therapeutic fluid is insulin.

17. A device according to claim 1, wherein the exit port assembly includes a transcutaneous patient access tool.

18. A device according to claim 17, wherein the transcutaneous patient access tool comprises a needle.

19. A device according to claim 1, further comprising a local processor connected to ends of the shape memory element through conductive wires and programmed to provide charges to the shape memory element based upon flow instructions.

20. A device according to claim 19, further comprising a power supply connected to the local processor.

21. A device according to claim 1, wherein:
    the side wall of the reservoir includes a first section extending from the outlet of the reservoir parallel with the longitudinal axis and a second section extending from the first section parallel with the longitudinal axis, and wherein the first section of the side wall has an internal cross-sectional dimension that is unequal to an internal cross-sectional dimension of the second section of the side wall; and
    the first and the second lateral segments of the plunger assembly are received in the second section of the side wall of the reservoir, and the plunger assembly further includes strut extending from the second lateral segment and slidingly received in the first section of the side wall of the reservoir, wherein the strut is sized and shaped to provided a substantially fluid-tight seal between the first section of the side wall and the strut.

22. A device according to claim 21, wherein the internal cross-sectional dimension of the first section of the side wall of the reservoir is smaller than the internal cross-sectional dimension of the second section of the side wall.

* * * * *

UNITED STATES PATENT AND TRADEMARK OFFICE
CERTIFICATE OF CORRECTION

PATENT NO. : 6,723,072 B2  Page 1 of 1
APPLICATION NO. : 10/163690
DATED : April 20, 2004
INVENTOR(S) : Flaherty et al.

It is certified that error appears in the above-identified patent and that said Letters Patent is hereby corrected as shown below:

Claim 1, column 17, line 4, after "material", insert --, wherein the lateral segments engage the sidewall to substantially prevent undesired longitudinal movement of the plunger assembly--.

Signed and Sealed this

Twenty-fourth Day of October, 2006

JON W. DUDAS
*Director of the United States Patent and Trademark Office*